United States Patent [19]
Antich et al.

[11] Patent Number: 5,197,475
[45] Date of Patent: * Mar. 30, 1993

[54] METHOD AND APPARATUS FOR ANALYZING MATERIAL PROPERTIES USING ULTRASOUND

[75] Inventors: Peter P. Antich, Richardson; James E. Dowdey, Arlington; Robert C. Murry, Jr., Irving, all of Tex.

[73] Assignee: The Board of Regents, The University of Texas System, Austin, Tex.

[*] Notice: The portion of the term of this patent subsequent to Aug. 13, 2008 has been disclaimed.

[21] Appl. No.: 717,025

[22] Filed: Jun. 18, 1991

Related U.S. Application Data

[63] Continuation-in-part of Ser. No. 230,845, Aug. 10, 1991, Pat. No. 5,038,787.

[51] Int. Cl.$^5$ ............................................. A61B 8/00
[52] U.S. Cl. ........................... 128/660.01; 128/660.08; 73/602
[58] Field of Search ..................... 128/660.01, 660.08; 73/602

[56] References Cited

U.S. PATENT DOCUMENTS

| | | | |
|---|---|---|---|
| 4,094,304 | 6/1978 | Wright | 73/574 X |
| 4,098,129 | 7/1978 | Deblaere | 73/599 |
| 4,361,154 | 11/1982 | Pratt | 128/774 X |
| 4,364,273 | 12/1982 | Redding | 73/614 |
| 4,421,119 | 12/1983 | Pratt | 128/774 X |
| 4,437,468 | 3/1984 | Sorenson et al. | 73/625 X |
| 4,457,311 | 7/1984 | Sorenson et al. | 73/625 X |
| 4,458,689 | 7/1984 | Sorenson et al. | 73/625 X |
| 4,476,873 | 10/1984 | Sorenson et al. | 73/625 X |
| 4,682,497 | 7/1987 | Sasaki | 73/602 |
| 5,038,787 | 8/1991 | Autich et al. | 128/660.01 |

OTHER PUBLICATIONS

Antich et al., J. Bone and Mineral Research, 6:417–426 (1991).
Antich et al., "A Novel Method for Characterizing Bone Strength at the Trabecular Level", Abstract 999, Journal of Bone and Mineral Research, 4 (Supplement): S367 (1989).
Zerwekh et al., "Intermittent Slow-Release Sodium Fluoride Therapy Produces Stronger Bone at the Microscopic Level", Abstract 998, Journal of Bone and Mineral Research, 4 (Supplement): S367 (1989).
Whiting, "Ultrasonic Critical Angle Reflection Goniometer for In Vitro Bone", Ultrasound in Medicine, 1629-1643 (Plenum: New York, 1977).
Mayer, Journal of Acoustical Society of America, 32:1213 (1960).
Mayer, Journal of Applied Physics, 34:909-911, (1963).
Lees, Ultrasonics, 213-215 (Sep., 1975).

(List continued on next page.)

Primary Examiner—Francis Jaworski
Attorney, Agent, or Firm—Arnold, White & Durkee

[57] ABSTRACT

Apparatus is disclosed for investigating the mechanical properties of a solid material such as bone, including means for positioning the apparatus in proximity to a surface of the material, at least one emitting ultrasound transducer, at least one receiving ultrasound transducer positioned to received ultrasound waves that have been emitted and have contacted the surface of the material, means for varying the angle of incidence of the emitted ultrasound wave towards the material, means for determining the alignment of the surface of the material with respect to the emitting and receiving ultrasound transdsucers, and signal analyzer means coupled to the receiving transducer for determining at least one characteristic of the received ultrasound wave which is indicative of a mechanical property of the material. A method is also disclosed of using such apparatus. The present invention permits the quick and efficient evaluation of treatment for osteoporosis, and whether that treatment has in fact reduced the tendency of a patient's bones to fracture.

38 Claims, 15 Drawing Sheets

OTHER PUBLICATIONS

Fountain, Journal of Acoustical Society of America, 42:242-247 (1967).
Mayer, Ultrasonics, 62-68 (Apr.-Jun., 1965).
Couchman et al., Ultrasonics, 69-71 (Mar., 1974).
Rollins, Journal of Acoustical Society of America, 44:431-434 (Feb., 1968).
Lees et al., J. Biomechanics, 5:557-566, (1972).
Weston-Bartholomew, Ultrasonics, 132-135 (May, 1973).
"Ultrasonic Bone Scanning Device", Biologue, p. 6 (1987-88).
Currey, Clinical Orthopedics and Related Research, 210-231 (Nov.-Dec., 1970).
Abendschein, Clinical Orthopedics and Related Research, 294-301 (Mar.-Apr. 1970).
Greenfield, Ultrasound, 115:163-166 (1975).
Greenfield, Radiation Physics, 138:701-710 (1981).
Craven, Investigative Radiology, 8:72-77 (1973).
Lees, Sonic Properties of Mineralized Tissues, Tissue Characterization with Ultrasound, Chap. 9, pp. 207-226 (1986).
Ashman et al., "Elastic Properties of Cancellous Bone: Measurement By An Ultrasonic Technique", 1986 SEM Spring Conference on Experimental Mechanics.
Ashman et al., J. Biomechanics; 17:349-361 (1984).
"Ultrasound Scanner Proving Effectiveness of Osteoporosis Drug", Center Times, p. 3 (May 1991).
Antich et al., "A Novel Technique for Assessing Mechanical Properties of Bone Material In Vitro By Ultrasound Reflection; Methodology and Comparison With Ultrasound Transmission", (in press).
Antich et al., "Measurement of Intrinsic Bone Strength In Vivo by Reflection Ultrasound; Correction of Impaired Strength With Slow Release Sodium Fluoride in Calcium Citrate", (in press).
Zerwekh et al, "Intermittent Slow-Release Fluoride Therapy Increases Material Strength of Bone as Assessed by Reflection Ultrasound Method", (in press).
Pak et al., "Fracture Incidence-Bone Density Relationship: A Reference for Interpreting the Effect of Slow-Release Sodium Fluoride Plus Calcium Citrate Treatement on Spinal Fracture Rate," (in press).

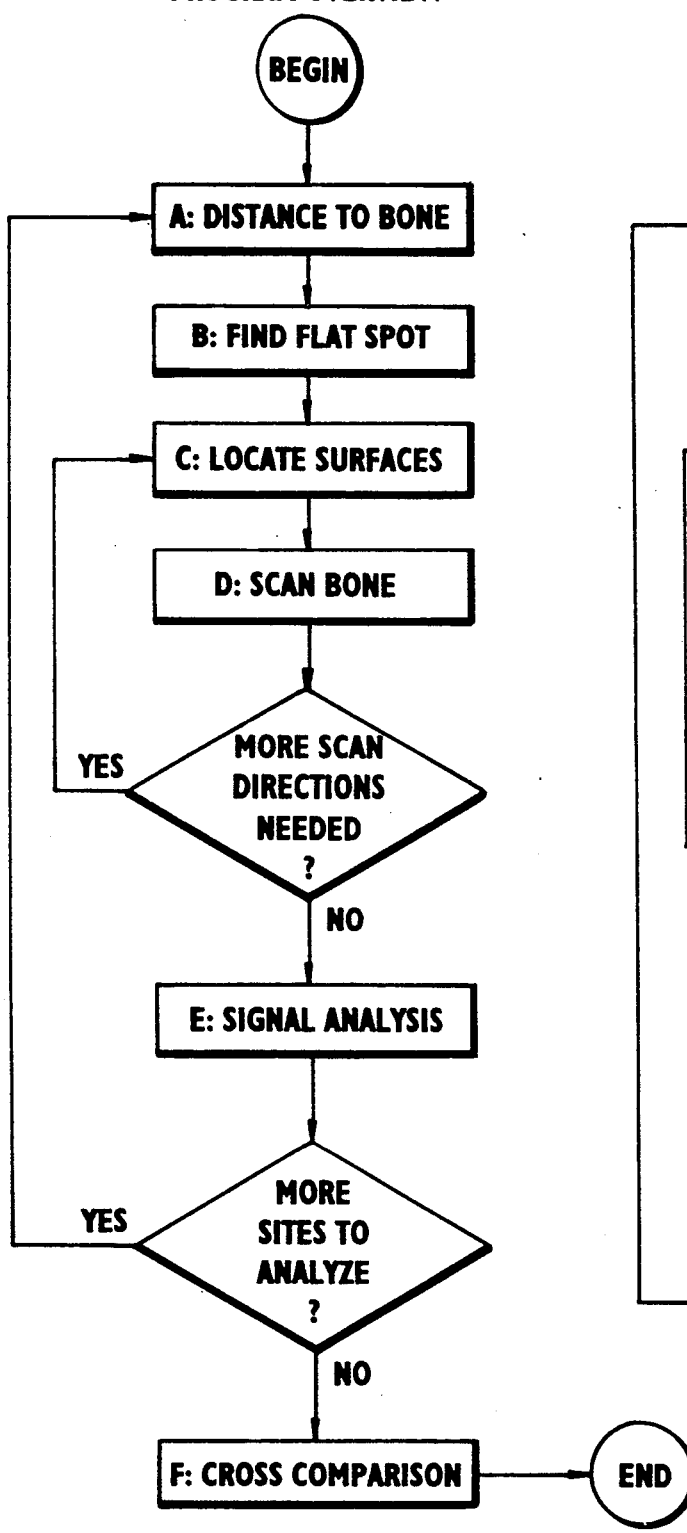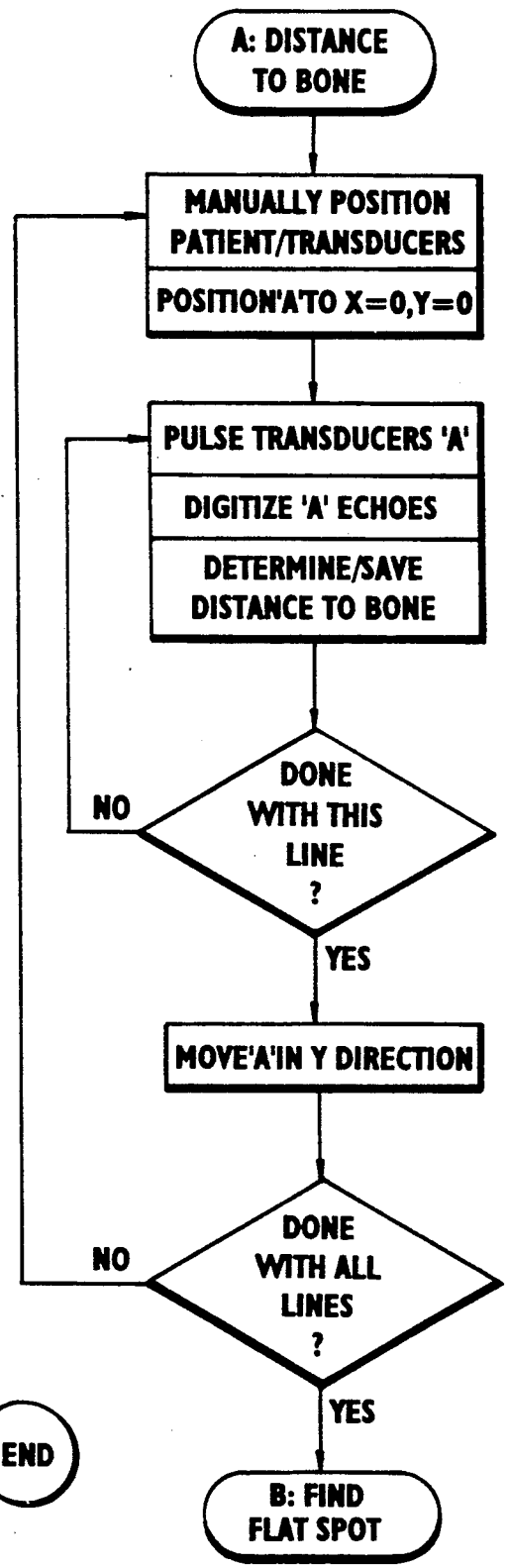
Fig. 5
Fig. 5A

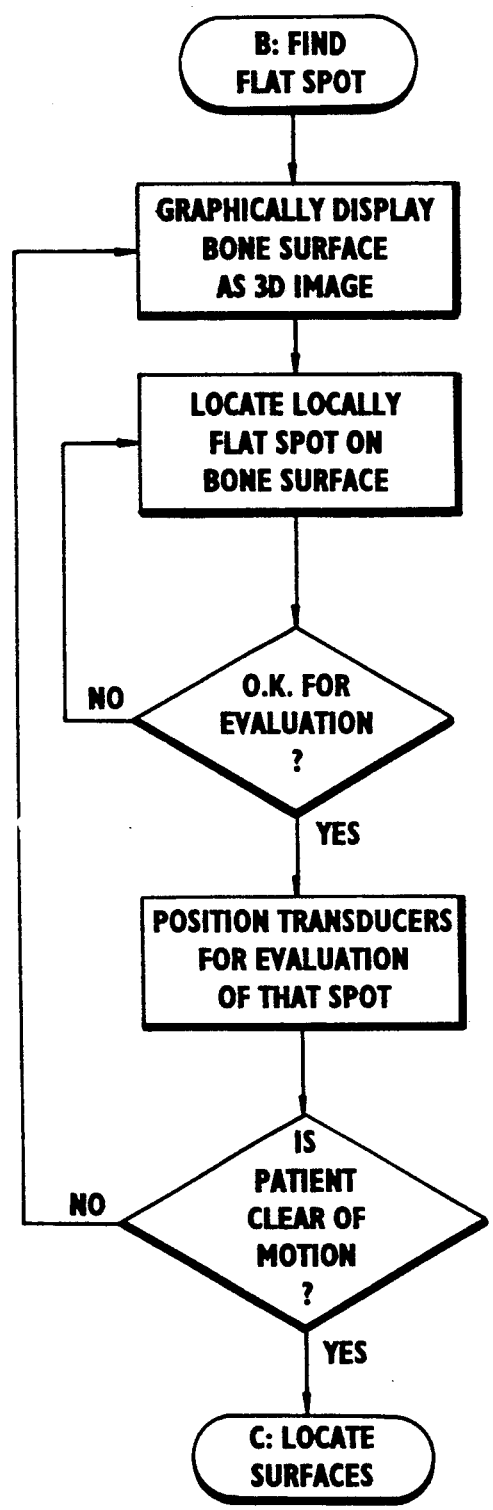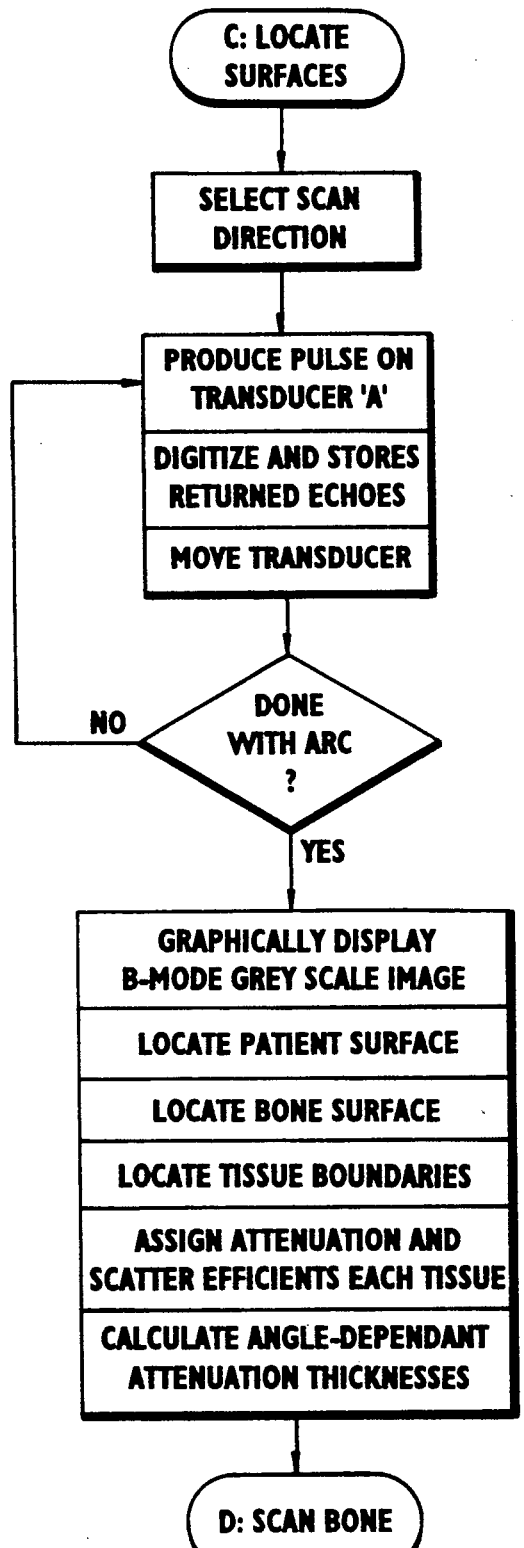
Fig. 5B
Fig. 5C

METHOD AND APPARATUS FOR ANALYZING MATERIAL PROPERTIES USING ULTRASOUND

This application is a continuation-in-part of U.S. Ser. No. 230,845, filed on Aug. 10, 1988, and now U.S. Pat. No. 5,038,787. That application is incorporated here by reference.

BACKGROUND OF THE INVENTION

This invention relates to a method and apparatus for determining the mechanical properties of a material, such as bone.

A number of situations arise where it is important to assess the mechanical properties of a material without destroying or damaging the material. In some cases, this can be done using simplified techniques as a result of the homogeneity of the material. However, in other cases, the material is not homogenous and therefore simplified techniques do not give accurate results.

For instance, in medical applications, it is frequently desirable to determine the mechanical properties of a material such as bone, but destructive tests of course cannot be used in a living patient. Further, invasive tests are undesirable, and the bone is nonhomogeneous and nonisotropic. These complications present a particular problem in the case of patients suffering from osteoporosis, who are more susceptible to fractures as a result of decreased bone strength. Standard radiographic properties of bone, such as bone mineral density, do not correlate well with bone strength, and therefore are of relatively little use in diagnosing osteoporosis or evaluating the results of treatment for that condition.

Although some treatments for osteoporosis are available that can increase the strength of a patient's bones, the utility of those treatments would be enhanced by a noninvasive method of assessing their effect on the patient's bones. In the past, various methods have been investigated for this purpose, but have failed to solve the problem. For example, radiologic methods such as quantitative computed tomography, single or dual photon absorptiometry, and dual energy X-ray absorptiometry measure the amount and distribution of minerals in bone, but do not directly assess its mechanical qualities. These problems of the prior art are minimized or solved by the method and apparatus of the present invention.

SUMMARY OF THE INVENTION

The present invention relates to apparatus for investigating the mechanical properties of a solid material, such as bone. The apparatus can include means for positioning the apparatus in proximity to a surface of a solid material, at least one emitting ultrasound transducer positioned for emitting an ultrasound wave towards the surface of the material, at least one receiving ultrasound transducer positioned for receiving ultrasound waves that have been emitted and have contacted the surface of the material, means for varying the angle of incidence of the emitted ultrasound wave towards the surface of the material, means responsive to the received ultrasound wave for determining the alignment of the surface of the material with respect to the emitting and receiving ultrasound transducers, and signal analyzer means coupled to the receiving ultrasound transducer for determining at least one characteristic of the received ultrasound wave which is indicative of a mechanical property of the material.

"Emitting" and "receiving" are intended to cover both embodiments in which the ultrasound wave is reflected from the material, and embodiments in which the ultrasound is transmitted through the material. In either case, the receiving ultrasound transducer receives the wave after it has contacted the material (i.e., reflected from the material or transmitted through it).

The apparatus preferably also includes means for varying the emitting plane which is defined by the emitted ultrasound wave and the normal to the surface of the material. The means for varying the emitting plane, as well as the means for varying the angle of incidence, can constitute a stepper mechanism which is coupled to the transducers, or, if the apparatus includes an array of transducers, can constitute a switching circuit for selectably operating at least one transducer in the array as an emitting transducer and at least one transducer in the array as a receiving transducer.

The signal analyzer means is preferably operable to determine at least one characteristic of the received ultrasound wave, selected from the group consisting of amplitude and phase of the received ultrasound wave. With respect to the amplitude of the received ultrasound wave, parameters such as maxima, minima (collectively referred to as "extrema"), and edges can be used to determine various velocities, and from that to estimate mechanical properties of the material. With respect to phase, parameters such as the angle of incidence at which phase first appreciably deviates from zero can likewise be used to estimate mechanical properties of the material.

The present invention also relates to a method of investigating the mechanical properties of a material, such as bone. The method includes the steps of emitting an ultrasound wave to impinge a surface of a material at an angle of incidence, receiving ultrasound waves after they have contacted the material, determining the normal to the surface of the material by analyzing the received ultrasound waves generated when the emitted ultrasound wave impinges the material from each of a plurality of varying directions, and determining a characteristic of the received ultrasound wave at each of a plurality of varying angles of incidence in the range of 0° to 90°, and in a plurality of varying emitting planes defined by the emitted ultrasound wave and the normal to the surface of the material, and using the characteristic to estimate a mechanical property of the material. The characteristic of the received ultrasound wave that is determined is preferably selected from the group consisting of amplitude and phase. Again, the received ultrasound wave can either be reflected from the material or transmitted through it.

The present invention provides the capability of determining the normal to the surface of the bone, which permits the use of a rational set of measurements to align the detectors and the bone. This is important because the normal defines the zero angle as well as the emitting plane (or plane of scattering), which must contain the normal and the incident wave (I). If the plane and zero were chosen incorrectly, the measurements obtained would be of little value as the angles would not be well measured. No known prior art procedure has this same capability.

In determining the normal, measurements could be taken in scattering planes some angle less than 90 degrees apart, such as 30 degrees apart; the smaller the incremental angle, the higher the accuracy and the precision of the method. Critical angles would be obtained for each plane. In an ex vivo use of the present invention, the bone sample would be rotated, while in clinical use with living patients, the applicator device (which would include the transducers) would be rotated while the patient remains stationary.

The advantages of the present invention are believed to be quite significant in evaluating the results of treatment for osteoporosis. Treatment of that condition can cause small variations in the material properties of bone (e.g., 2-5 percent change as a consequence of treatment over two years in representative experiments), and yet those small variations can correlate to clinically significant improvements in the resistance of the bone to fracture. Therefore, the present invention provides a much more accurate and useful means of evaluating the effect of osteoporosis treatment than any known prior art ultrasound apparatus.

BRIEF DESCRIPTION OF THE DRAWINGS

FIG. 5 is a flow chart of the application software for the computer of FIGS. 3 and 4, where:

FIG. 5A describes the "Distance to Bone" subroutine,

FIG. 5B describes the "Find Flat Spot" subroutine,

FIG. 5C shows the "Locate Surfaces" subroutine,

DESCRIPTION OF THE PREFERRED EMBODIMENTS

The method and apparatus of the present invention are useful in determining the physical properties of a variety of materials. Because the present invention relies on ultrasound waves, the only material requirements are that the material under investigation reflect and/or transmit a significant ultrasound component, and that the velocity of sound in it be greater than that of the first medium (e.g. water or soft tissue).

Figure 1:
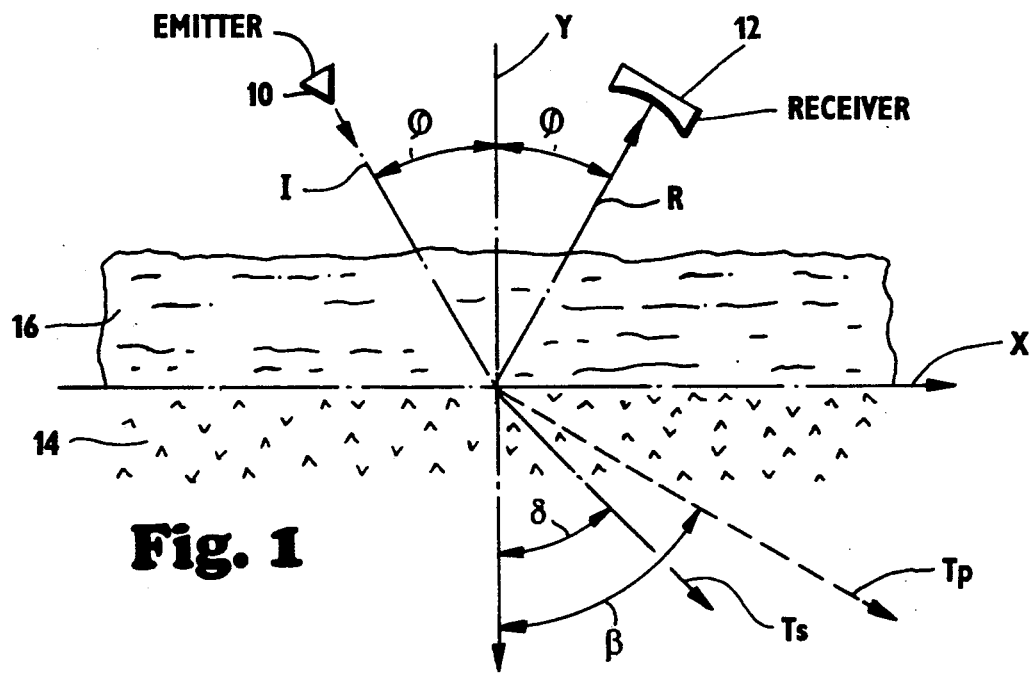
FIG. 1 is a schematic view of the propagation patterns of the ultrasound waves in the method of the present invention.
Figure 2:
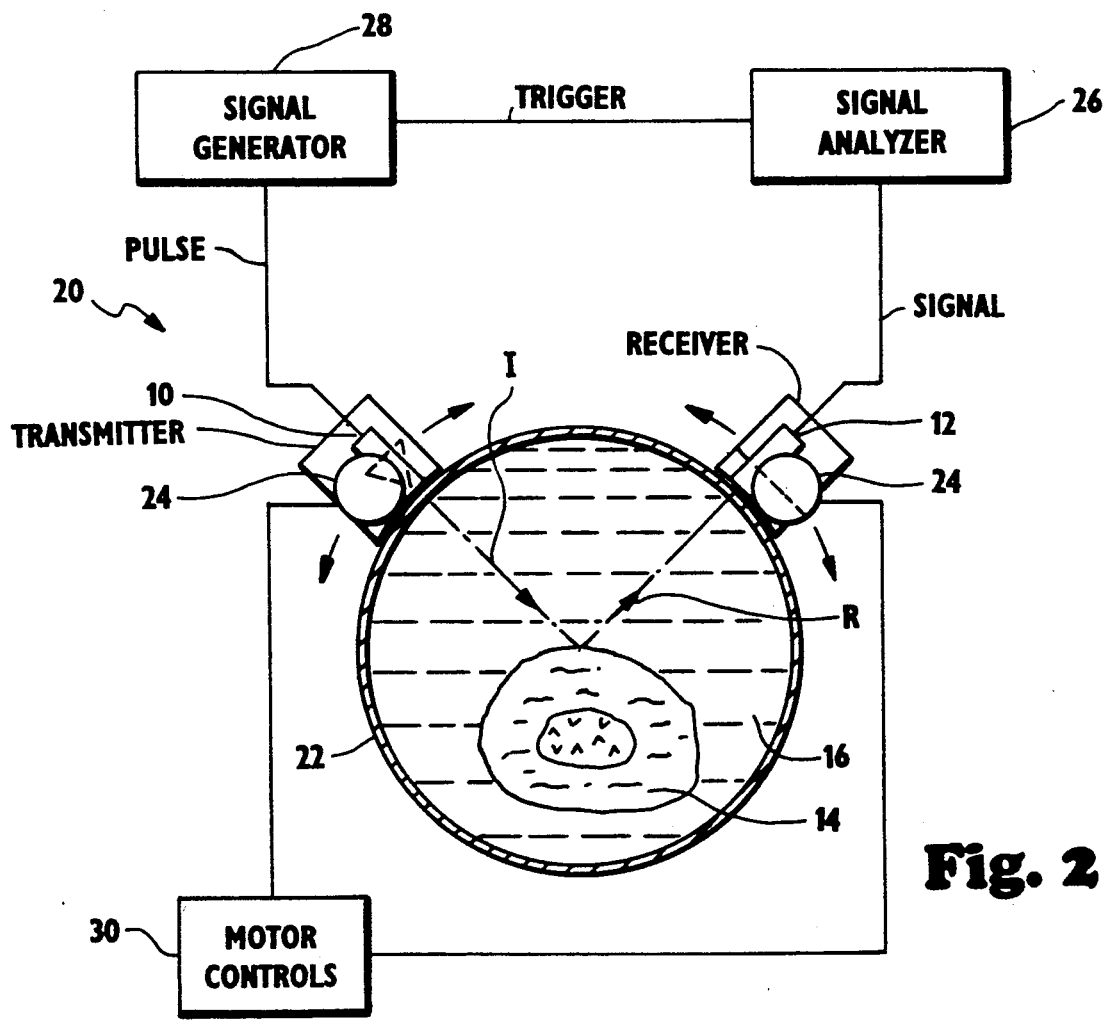
FIG. 2 is a schematic view of an apparatus in accordance with the present invention.
Figure 3:
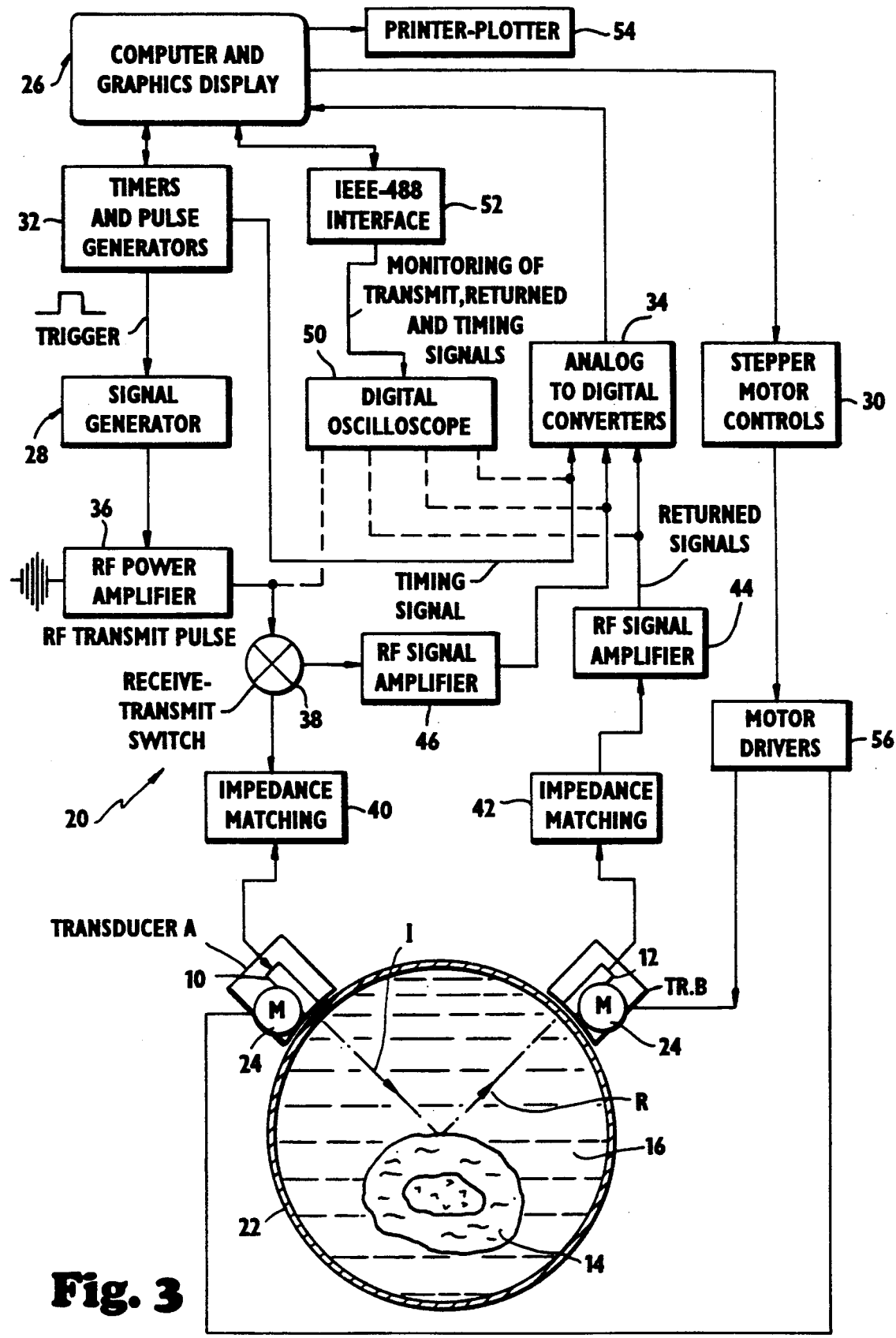
FIG. 3 is a schematic view showing in block diagram the components of an embodiment of the apparatus of the present invention.
Figure 4:
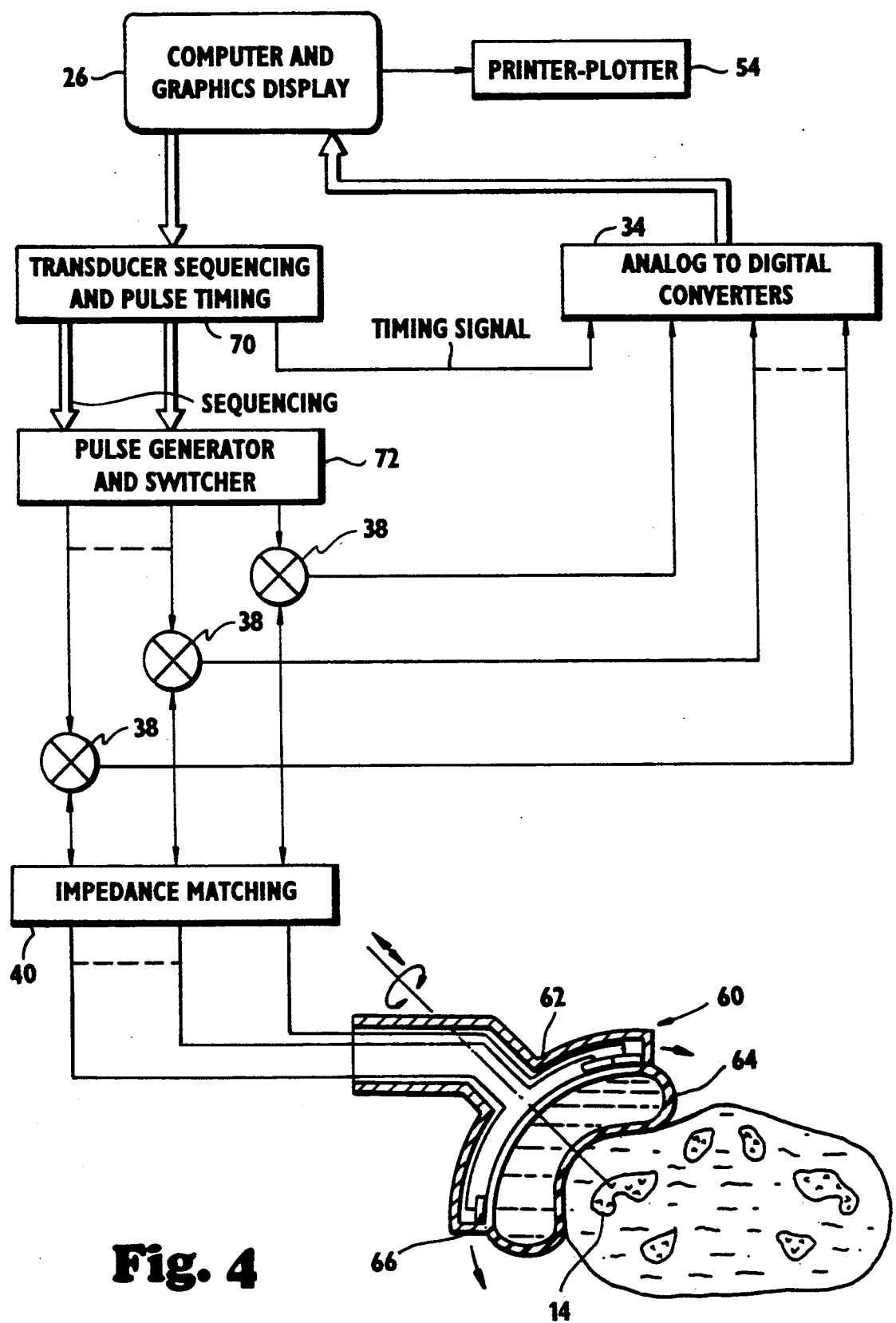
FIG. 4 is a schematic view showing in block diagram an alternative embodiment of the apparatus of the present invention.

FIGS. 1 and 2 illustrate the general critical angle of reflection method of the present invention and are useful in understanding the specific embodiments of FIGS. 3-5. FIG. 1 illustrates an ultrasound transducer 10 functioning as an emitter or transmitter and an ultrasound transducer 12 functioning as a receiver. An ultrasound wave (I) impinges upon a plane separating the material under investigation 14 (such as bone) from a separating medium 16 (such as soft tissue). For convenience, the plane defined by the direction of propagation of the transmitted wave and the normal to the surface of the material 14 is defined as the XY plane in FIG. 1. The incoming or transmitted wave (I) upon arrival at the interface of the material 14 and medium 16 (YZ plane with X=0) gives rise to a reflected wave (R) redirected through the medium 16 to the receiving transducer 12. For illustrative purposes, particle motion in FIG. 1 is seen to be constrained to the XY plane, so that the transmitted wave (I) gives rise to a pressure wave $T_p$ and shear wave $T_s$. The angle of refraction of the pressure wave $T_p$ is denoted as $\beta$, while the angle of refraction of the shear wave $T_s$ is $\gamma$. In FIG. 1, the angle of incidence of the transmitted wave (I) is $\phi$, and in a preferred embodiment the angle of reflection of the reflected wave (R) is about equal to the angle of incidence $\phi$.

In an alternate embodiment, the transmitted wave (I) contacts the material 14 and is transmitted through the material, with the receiving transducer 12 located on the opposite side of the material.

The amplitudes of the displacement velocities corresponding to the pressure wave $T_p$ and shear wave $T_s$ are determined by conservation laws, which take into account the properties of material 14 and medium 16 as follows:

(1) continuity of normal components of the displacement (displacements along the normal are equal on each side of the interface);

(2) continuity of normal components of the stresses;

(3) continuity of the normal components of the intensity vector (absence of energy absorption at the interface); and (4) constant phase relationship between waves along the entire wave front.

Obeying such conservation laws, from FIG. 1 the angles are related by the following condition:

$$\frac{\sin \phi}{c} = \frac{\sin \beta}{v_p} = \frac{\sin \gamma}{v_s}$$

where c is the velocity of the transmitted wave (I) in the medium 16, $v_p$ is the velocity of the pressure wave $T_p$, and $v_s$ is the velocity of the shear wave $T_s$ in the material 14.

At a certain angle of incidence $\phi$, $T_p = T_s = 0$, and therefore all the wave energy is reflected (reflection is a maxima, R=1). This angle of incidence is referred to as the first critical angle $\phi_1$, and is useful in the method of the present invention.

A second critical angle ($\phi_2$) occurs when the transmitted shear wave vanishes ($T_s = 0$) and the absolute value of the reflected wave (R) is at or near a maximum. This second critical angle is greater than the first critical angle $\phi_1$, but is still less than 90°. At this angle, the amplitude $T_p$ represents a surface wave traveling parallel to the surface of the medium 16. $\phi_2$ occurs either at a maximum ($R_2$ positive) or at an inflection point ($R_2$ negative). In this latter case, $\phi_2$ falls between a zero (minimum) and a maximum.

Turning to FIG. 2 the schematic of an apparatus 20 in accordance with the present invention is illustrated. Broadly speaking, the apparatus 20 includes a means for emitting or transmitting an ultrasound wave (transducer 10) and a means for receiving the reflected ultrasound wave (transducer 12). (In an embodiment where the system uses transmitted ultrasound rather than reflected ultrasound waves, the receiving transducer 12 would be positioned on the opposite side of the material 14 from the transmitting transducer 10.) A holding mechanism 22 positions the material under examination, while the separating medium 16 is interposed between the material 14 and transmitter and receivers 10 and 12. In FIG. 2, the material 14 under examination is a bone, while the separating medium 16 includes water and soft tissue.

A stepping motor 24 is coupled to transmitter 10 and receiver 12 respectively, and is coupled to the holding mechanism 22 by a toothed circular rail (not shown). The stepping motors are operable through motor controls 30 to move the transmitter 10 and receiver 12 through an arc about the material 14.

The signal analyzer 26 is preferably a microcomputer, which periodically triggers the signal generator 28. Upon receiving the trigger, the signal generator 28 generates a pulse which is amplified and passed to the transmitter 10. The transmitter 10 upon receiving the pulse transmits the ultrasound wave (I) through the medium 16 towards the material 14. The receiver 12 receives the ultrasound wave (R) reflected by the material 14 (or transmitted through the material 14 in an alternate embodiment). Preferably the transmitter 10 and receiver 12 are tuned to the same frequency.

During examination, the transmitter 10 and receiver 12 are initially positioned close to the normal to the material 14 (adjacent the Y axis as shown in FIG. 1). The transmitter 10 and receiver 12 are simultaneously stepped about the holding mechanism 22 so that the angle of incidence of the transmitted wave (I) is equal to the angle of reflection of the reflected wave (R). As shown in FIG. 1, this angle is denoted $\phi$ and preferably increases in the range from 0°-90°, but useful investigations may be conducted using a more restricted range, e.g. to include only the first critical angle. As can be appreciated from FIG. 2, after each ultrasound transmitted wave (I), the motor controls 30 simultaneously step the transmitter 10 and receiver 12 to a new position. Depending upon the number of measurements desired (i.e. resolution), the transmitter 10 and receiver 12 are preferably stepped in increments of a fraction of a degree. Thus, the receiver 12 generates a signal at each increment which is recorded by the signal analyzer means 26 and represents the amplitude of the reflected wave (R) for a corresponding angle $\phi$. The result of this examination is a plot of reflected amplitude (ordinate) versus the angle of incidence $\phi$ (abscissa).

Turning now to FIG. 3, an embodiment of the apparatus 20 of the present invention is illustrated in more detail. In the embodiment of FIG. 3, the transmitting transducer 10 is used as a signal transceiver, while the receiving transducer 12 is used as a receiver only. The microcomputer 26 periodically generates a trigger signal through the timer and pulse generator 32. The timer 32 generates a trigger to the signal generator 28 as shown in the drawing, and additionally generates a signal which is simultaneously passed to the analog-to-digital converters 34. The signal generator 28 generates a signal which is amplified by RF power amplifier 36, with the amplified signal passing through transmit switch 38 to the impedance matching network 40.

As can be appreciated from FIG. 1, the ultrasonic wave pressure from the transmitted wave (I) is reflected from the material surface 14 as reflected wave (R) and received by the receiver 12. The receiver 12 transforms the reflected wave (R) into a return signal which is passed through an impedance matching network 42, amplified at power amp 44, and presented to the A to D converters 34 as a return (retarded) pulse. The A to D converters 34 generate a digital signal which is representative of the analog return signal from transducer 12. As can be appreciated, if the transducer 10 is operated as a receiver, the switch 38 is toggled and the return signal amplified by the power amp 46 and presented to the A to D converters 34 in a similar fashion.

Digital oscilloscope 50 is used as needed and can be coupled as shown to the various circuits to verify, quantify and test signals in these circuits. Thus, the digital oscilloscope can monitor the amplified signal from the power amplifier 36, the return signals from the amplifiers 44 and 46, as well as the timing pulse from the timer 32. The signals monitored by the digital oscilloscope 50 may be graphically presented through the IEEE-488 interface 52 on the graphic display of the computer 26. A printer/plotter 54 is provided as an output option from the computer 26.

The stepper motor controls 30 receive inputs from the computer 26 as shown to incrementally step the transducers 10 and 12 about the material 14. As can be seen, the motor drivers 56 sense the input from the motor control 30 to synchronously, but independently, actuate the respective stepping motors 24 to move the transducers 10 and 12. The transducers 10 and 12 are preferably moved in incremental steps of fixed value and are at the approximately identical angle of incidence $\phi$ for each increment.

The holding mechanism 22 is adaptable for different uses, primarily dependent upon its size. For example, in the preferred embodiment of FIG. 3 a small, laboratory size system has been used for holding a single sample of polished bone or other material 14 in the water medium 16. This holding mechanism 22 has been found useful not only for experimental verification, but also for ex vivo analysis of samples and biopsies. Alternatively, a clinical system of the holding mechanism 22 has been devised in which the holding mechanism 22 is sufficiently large to receive portions of the human skeletal structure. This clinical system may be used for in vivo or in situ analysis and diagnosis of the tendency of bone to fracture, of bone healing, etc. Of course, different types of holding mechanisms 22 may be devised for holding different types of materials 14 other than bone.

Turning to FIG. 4, a block diagram of an alternative embodiment is illustrated in which the transducers are fixed and the transmission and reception are controlled electronically rather than mechanically as illustrated in FIG. 3. In FIG. 4, in situ analysis of a material 14 (bone) is illustrated. A transceiver system 60 includes an applicator head 62 which is capable of three dimensional adjustment motion (as shown by the direction arrows in FIG. 4). Although the applicator head 62 of FIG. 4 is manually adjustable, computer adjustment control is a desirable alternative. As can be seen, a pressurized, temperature controlled water bag or water bolus 64 is interposed between the applicator head 62 and patient, assuring good contact and match with the surface of the body of the patient. The water bag 64 has at least one surface that is flexible and can be positioned on the surface of a human body in proximity to a bone. The ultrasound transducers are in acoustic contact with the water bag. For example, the transducers can be immersed in the bag, or can be external to the bag but contacting it such that the ultrasound is conducted through the bag to or from the transducers. The applicator head 62 is positioned so that its focal point on the bone surface and its axis is aligned with the axis of the normal to the bone surface 14 at the point of interest as illustrated in FIG. 4.

The transceiver system 60 incorporates a circular transducer array comprising eighty small ($\frac{1}{4}$ inch by $\frac{1}{4}$ inch) transducers 66. As can be appreciated, with the transceiver system 60 positioned in a desired location adjacent the patient, the transducers 66 can be electronically activated alternatively as transmitters or receivers as desired. Preferably, the transducers 66 are sequentially activated one at a time as a transmitter, or may be activated in a small group to give better definition of sound wave as it intersects with the bone 14. After a transducer 66 pulse, the transducers will be switched to act as receivers for the reflected sound energy of the reflected wave (R).

Sequence and timing mechanism 70 is provided which upon receiving a trigger signal from the computer 26 selects which transducer 66 (or group of transducers) will be pulsed and the duration of the pulse. The timing signal at the beginning of the pulse is also supplied to the A/D converter section 34. The pulse generator and switcher 72 generates and amplifies the signal which is directed through a specific lead line and switch 38 and impedance matching network 40, to a specific transducer 66 (or group of transducers). As soon as the transmitted wave (I) is generated from the activated transducer 66, the pulse generator and switcher 72 toggles the switches 38 to convert the transducers 66 to receive operation. Thus, all eighty transducers are acting as receivers for the reflected wave (R). The return signals indicative of the reflected wave (R) will pass through the A/D convertors 34, digitized, and presented to the computer 26 for processing and presentation.

Figure 5D:
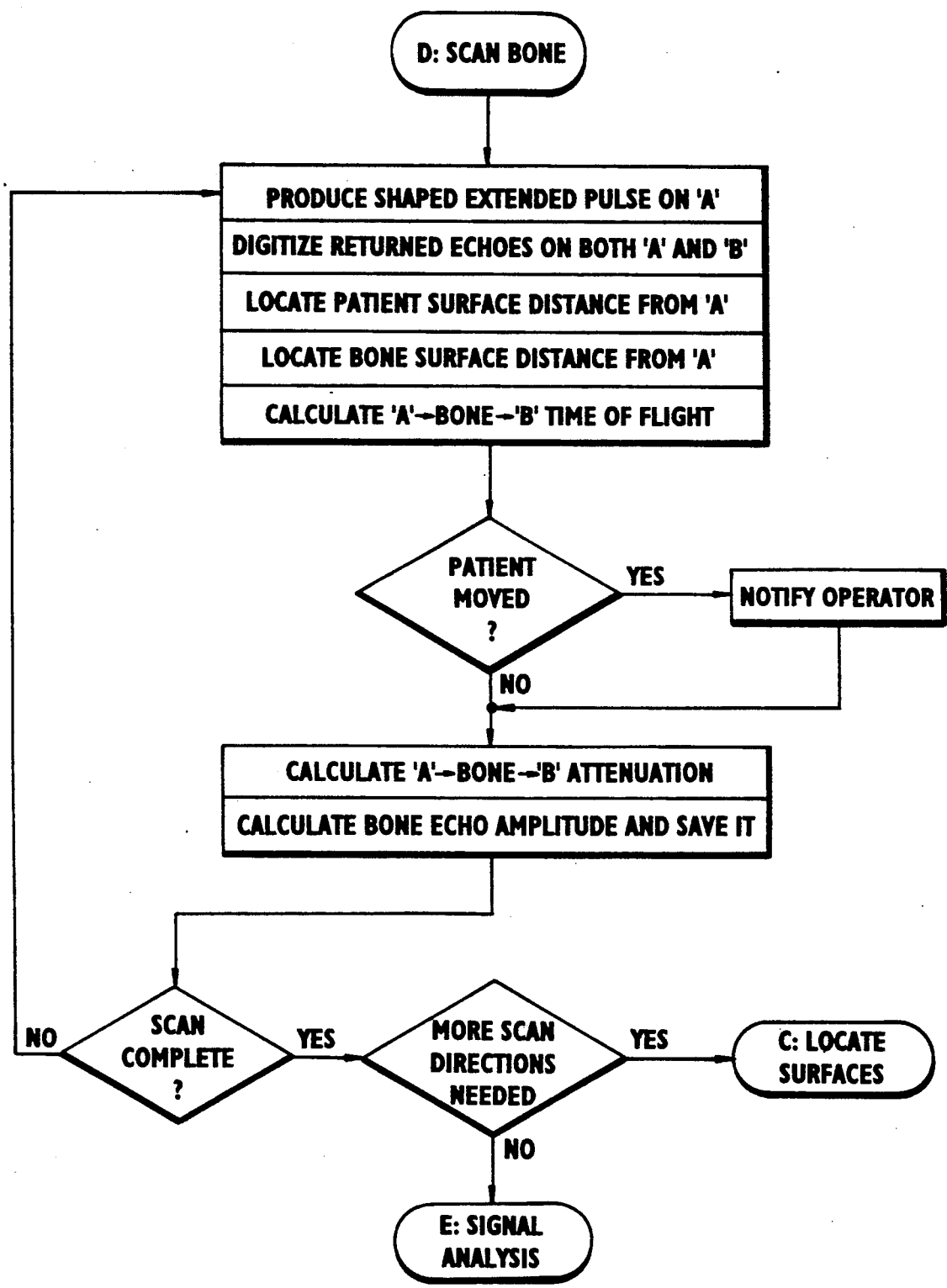
FIG. 5D illustrates the "Scan Bone" subroutine.
Figure 5E:
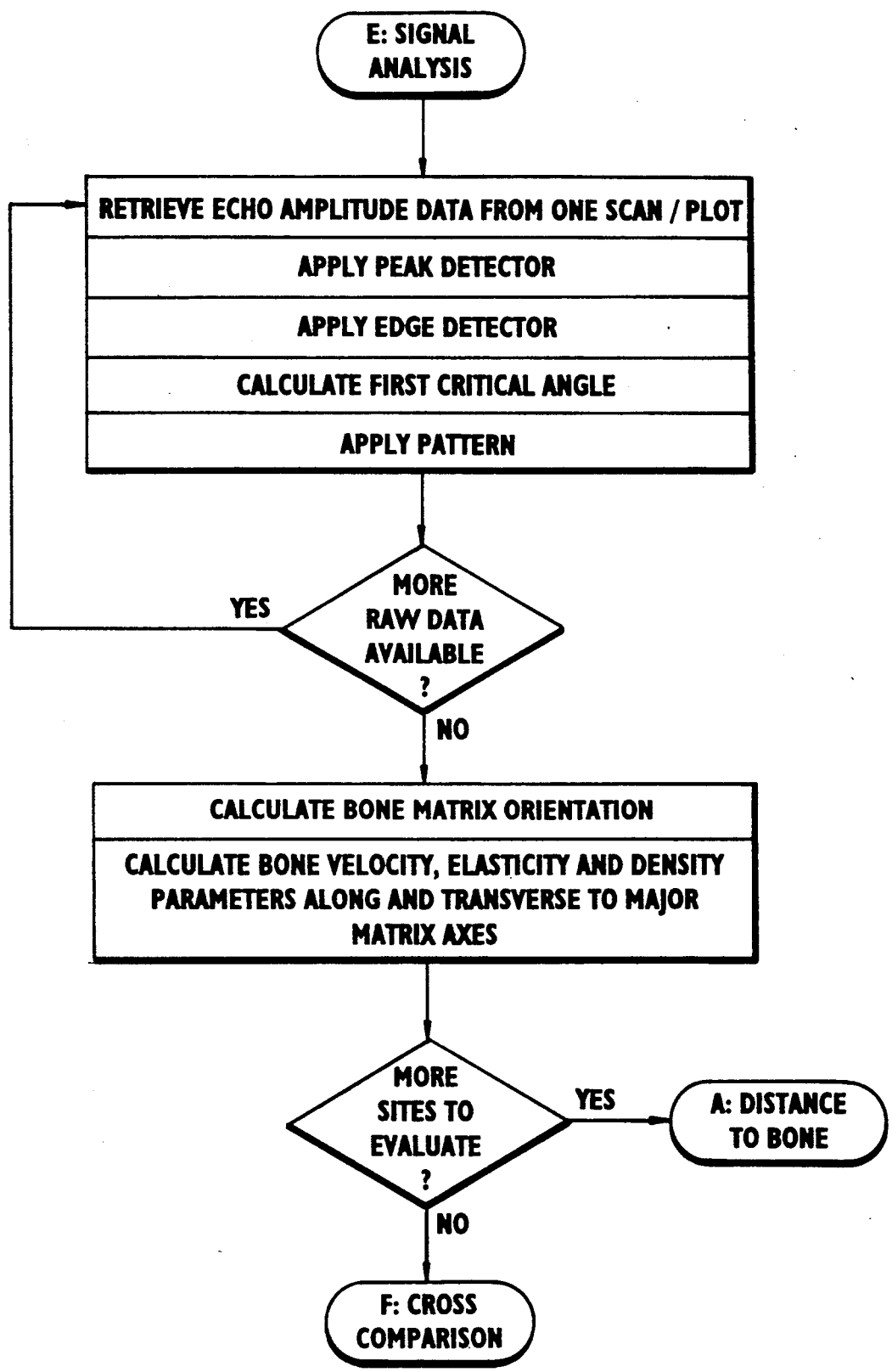
FIG. 5E describes the "Signal Analysis" subroutine.
Figure 5F:
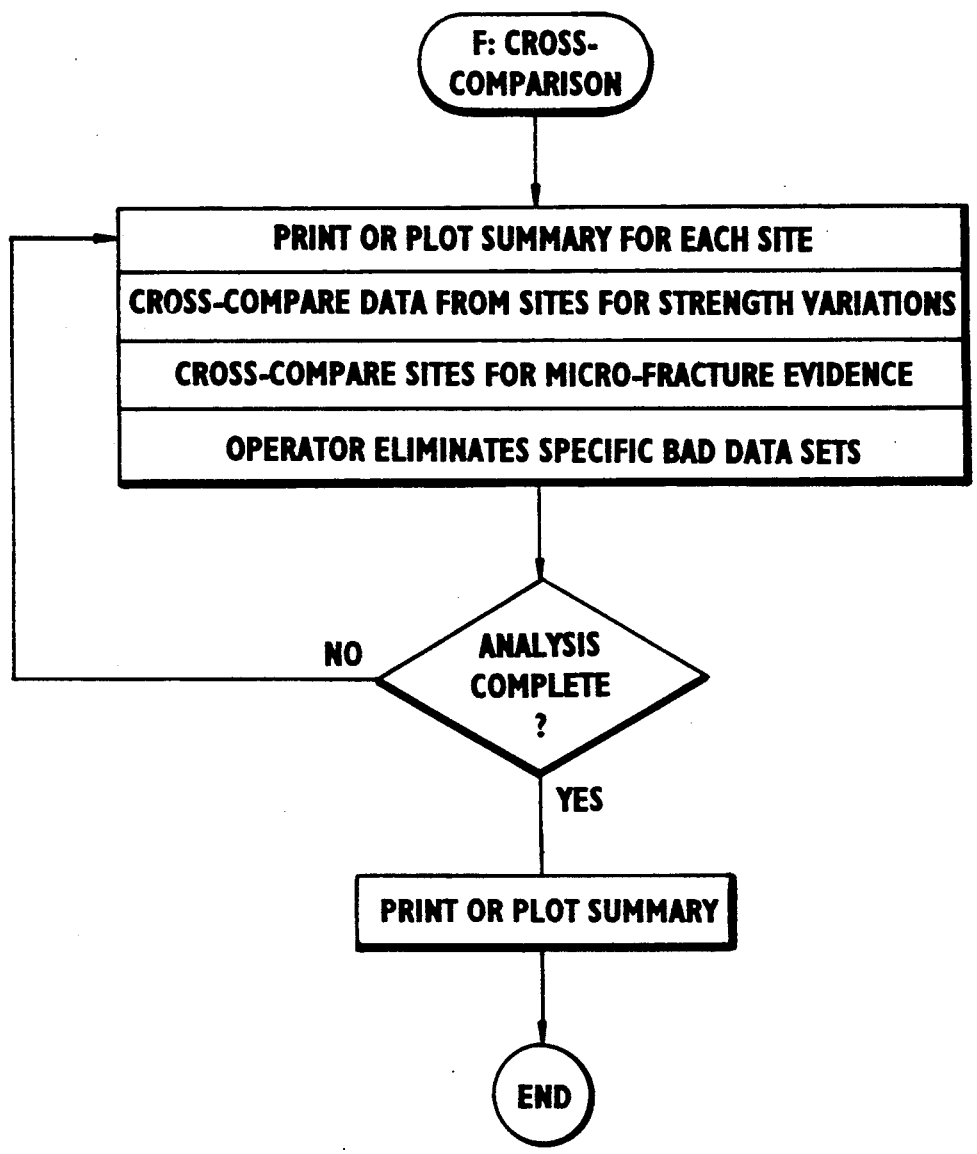
FIG. 5F illustrates the "Cross Comparison" subroutine.

FIG. 5 represents the flow charts for the operating software of the computer 26 of FIG. 3. FIG. 5 illustrates the main program or program overview, while FIGS. 5A–5F illustrate the subroutines as indicated. As can be seen from FIGS. 5 and 5A, the first subroutine is designed to determine the distance from the transducer 10 (or transducer "A") to the bone 14. This is easily accomplished using the apparatus 20 of FIG. 3, by operating the transducer 10 alternately in the transmit and receive mode. As can be seen from FIG. 5A, the patient or bone 14 is first manually positioned in the holding mechanism 22 and the transducer 10 manually positioned in a direct vertical orientation to the bone as viewed in FIG. 3. The transducer 10 is then pulsed and the echoes received with the lapsed time determinative of the distance to the bone 14. Distance to the bone can be calculated for each incremental increase in the angle of incidence $\phi$ (transducer 10 positioned in the arc about bone 14 as in FIG. 2 or by moving the applicator head 62 as in FIG. 4).

After the completion of subroutine 5A, the program proceeds to subroutine "Find Flat Spot" as illustrated in FIG. 5B. The distance to the bone calculated at various increments from the subroutine "Distance To Bone" are graphically displayed as an image on the computer 26 and correlated to find a relatively smooth, flat spot for evaluation. Once such a relatively flat spot is located, patient movement is prohibited and the transducers are positioned for evaluation of the flat spot, i.e. at a distance such that this spot is at the center of rotation and taking the normal to the flat spot as the axis of symmetry of transducer motion in a given plane (direction). The direction of the plane can be varied.

The program's next step is the subroutine "Locate Surfaces" illustrated in FIG. 5C, which is designed to locate the surfaces separating various media (tissues) which intervene between the transducers and bone surface. The transducer 10 is first positioned at a relatively small angle of incidence $\phi$ and the transmitted signal (I) initiated (pulsed). The reflected signal (R) is received, digitized, and stored on computer 26 before stepping the transducer 10 in the arc about the bone 14. Note from FIG. 5C that after the arc is completed and the digitized amplitude of the echo return signals stored, the various patient tissues are identified. That is, the patient surface, bone surface, and other intervening tissue boundaries (muscle, fat) are located, attenuation and scatter coefficients are assigned for each respective tissue, and the angle dependent attenuation thicknesses and beam path calculated. Thus, the "Locate Surfaces" subroutine primarily identifies the intervening tissue boundaries so that tissue attenuation and the ray path followed by the incident and reflected waves can be identified.

The next subroutine is illustrated in FIG. 5D and performs the "Scan Bone" routine to generate the primary raw data. As can be seen in FIG. 5D, the transmitted wave (I) is generated and the reflected wave (R) is received for each increment in angle of incidence $\phi$. The distance from transducer 10 to the patient surface and bone surface is retrieved and the time of flight calculated for both the transmitted wave (I) and reflected wave (R). These are compared to the information obtained in the previous routine to check for patient movements. If no movement occurred, the "Scan Bone" subroutine then calculates bone echo amplitude corrected for attenuation in the intervening tissues and stores the digitized echo amplitude. The "Scan Bone" subroutine loops until the scan is complete. If more scans at the same site but along different directions are desired, the program loops back to "Locate Surfaces" until all desired scan directions are completed. Once all selected scan sites and scan directions are completed, the signal analysis (FIG. 5E) is initiated.

Turning to FIG. 5E, the "Signal Analysis" subroutine is depicted. The stored amplitude data as a function of angle of incidence $\phi$ is retrieved for a particular scan, and peak and edge detector algorithms applied. The first peak or "maxima" detected identifies the first critical angle. Preferably, the second critical angle is also identified as a second maxima following the first maxima. The "Signal Analysis" subroutine then calculates the bone matrix orientation, various bone velocities along major axes (shear velocities and pressure velocities), and the matrix of coefficients of elasticity (Young's and Poisson's modulus for isotropic materials), and density. If more sites are to be evaluated, then the program is repeated by returning to the "Distance To Bone" subroutine (FIG. 5A). However, if the sites have all been evaluated, the "Cross Comparison" subroutine of FIG. 5F is entered.

In alternative embodiments, the "Signal Analysis" subroutine can also use data on the phase of the reflected wave as a function of angle of incidence, or data on the amplitude of a wave transmitted through the bone.

As can be seen from FIG. 5F, the user has several options for generating hard copy record on the printer/plotter 54. First, the user may plot the mechanical properties summary for each site—that is the bone matrix orientation, velocity, matrix of elasticity, and density. Next, the user may cross compare mechanical properties for the different sites for which data has been taken to look for strength variations. Microfracture evidence may be readily compared at different sites. Finally, the summary can be printed or plotted.

In one embodiment of the method of the present invention, the velocity of sound in a solid material is measured by observing the angular dependence of the amplitude of an ultrasound wave reflected from a solid sample. When an ultrasound beam travelling in water arrives at a water-solid interface, it gives origin to reflected and refracted waves. The reflected wave in water propagates at the same angle as the incident wave (angle of incidence). In isotropic solids there are, in general, both pressure and shear refracted waves, which propagate at angles typically larger than the angle of incidence. The reflected amplitude is greatest when the angle of refraction for the pressure wave equals 90°. When this occurs, the angle of incidence is said to reach its critical value $\phi_c$. From this, the velocity of sound in the material, $V_r$, is computed using Snell's law:

$$V_r = \frac{c}{\phi_c}$$

where c is the velocity of sound in water.

When a reflected ultrasound wave is received in the method of the present invention, in one embodiment of the invention, the amplitude of the reflected wave is determined as a function of the angle of incidence. If the first maxima (first critical angle) in this function is determined, it can be used to determine the velocity of the pressure wave in the solid material, using the formula:

$$v_p = \frac{c}{\sin\phi_1}$$

The pressure wave velocity can also be determined based on the angle of incidence ($\phi^\epsilon$) at which the amplitude has an inflection point in an edge region, along with the angular width ($\omega$) of the beam at that point, using the relationship $$v_p = \frac{c}{\sin\left(\phi_2^\epsilon - \frac{\omega}{2}\right)}$$

Similarly, the shear wave velocity in the material can be determined based on the second critical angle (which corresponds to either a second maxima in amplitude followed by a deep minimum, or to an inflection point in the amplitude following a deep minimum and encountered after the first maxima as the angle of incidence increases in the range 0–90°), using the formula $$v_s = \frac{c}{\sin\phi_2}$$

or based on the second edge ($\phi_2^\epsilon$) in the amplitude function as the angle of incidence increases, using the formula:

$$v_s = \frac{c}{\sin\left(\phi_2^\epsilon - \frac{\omega}{2}\right)}$$

The second edge is further characterized by the fact that it precedes a deep minimum in amplitude.

Alternatively, the shear wave velocity can be determined based on the angle of incidence ($\phi_{180}$) at which the phase is equal to 180°, using the formula:

$$v_s = \frac{c}{\sin\phi_{180}}$$

or based on the angle ($\phi^N$) at which the phase exhibits a sharp increase in the rate of change of amplitude, using the formula:

$$v_s = \frac{c}{\sin\phi^N}$$

or on both of these parameters.

In another embodiment, the phase of the reflected wave is determined as a function of the angle of incidence. In this embodiment, at least one angle ($\phi_\Delta^1$) is determined at which the phase first appreciably deviates from zero as the angle of incidence is increased from 0°. This information can be used to determine or estimate the pressure wave velocity by means of the formula:

$$v_p = \frac{c}{\sin\phi_\Delta^1}$$

Additionally, an angle of incidence ($\phi_\Delta^2$) can be determined at which the phase changes rapidly, and can be used to determine the shear wave velocity using the formula:

$$v_s = \frac{c}{\sin\phi_\Delta^2}$$

When a transmitted wave is received in another embodiment of the invention, the amplitude of the transmitted wave is determined as a function of the angle of incidence, and at least two minima ($\phi_t^1$ and $\phi_t^2$) are determined, to be used in determining or estimating the pressure and shear wave velocities, by means of the formulae:

$$v_p = \frac{c}{\sin\phi_t^1}$$

$$v_s = \frac{c}{\sin\phi_t^2}$$

The reflected ultrasound signal can be used to determine the density ($\rho_m$) of the material based on the angle of incidence ($\phi_{90}$) at which the phase is equal to 90° using the formulae:

$$x = \sin\phi_{90}$$

$$\rho_m = \frac{1}{4\cos\phi \cdot v_p \cdot \left[ \frac{(v_s^2 x^2 - 0.5)^2}{\sqrt{v_p^2 x^2 - 1}} - v_s^3 x^2 \sqrt{v_s^2 x^2 - 1} \right]}$$

In an embodiment in which phase is determined, it is preferred that it be determined over a range in which it varies from at least 0–90°, and preferably 0–180°.

Figure 6:
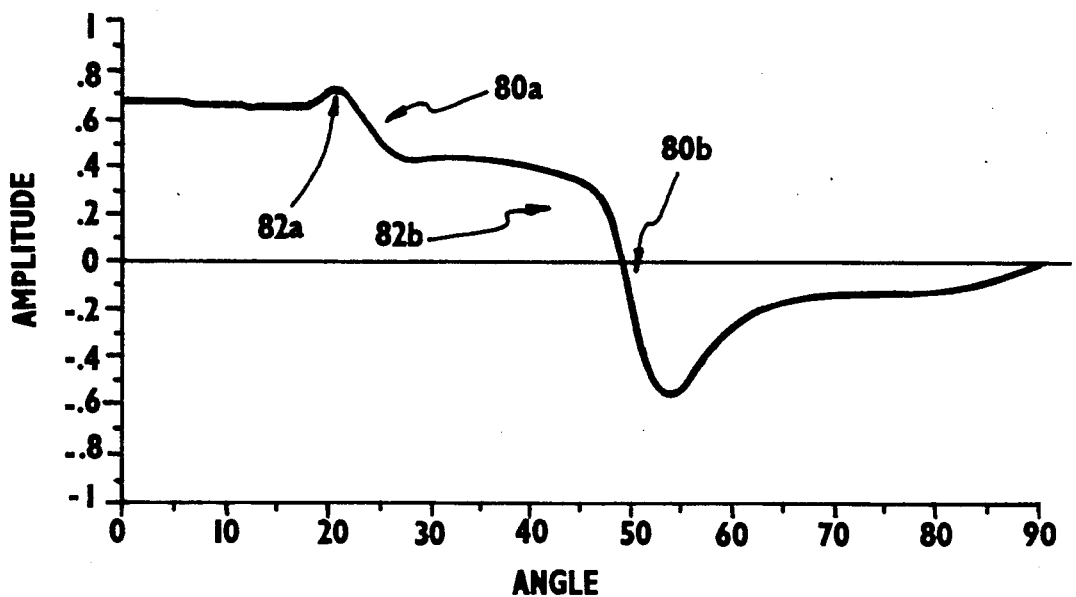
FIG. 6 is a graph of the amplitude of a reflected ultrasound wave in the method of the present invention as a function of angle of incidence of the emitted wave.
Figure 7:
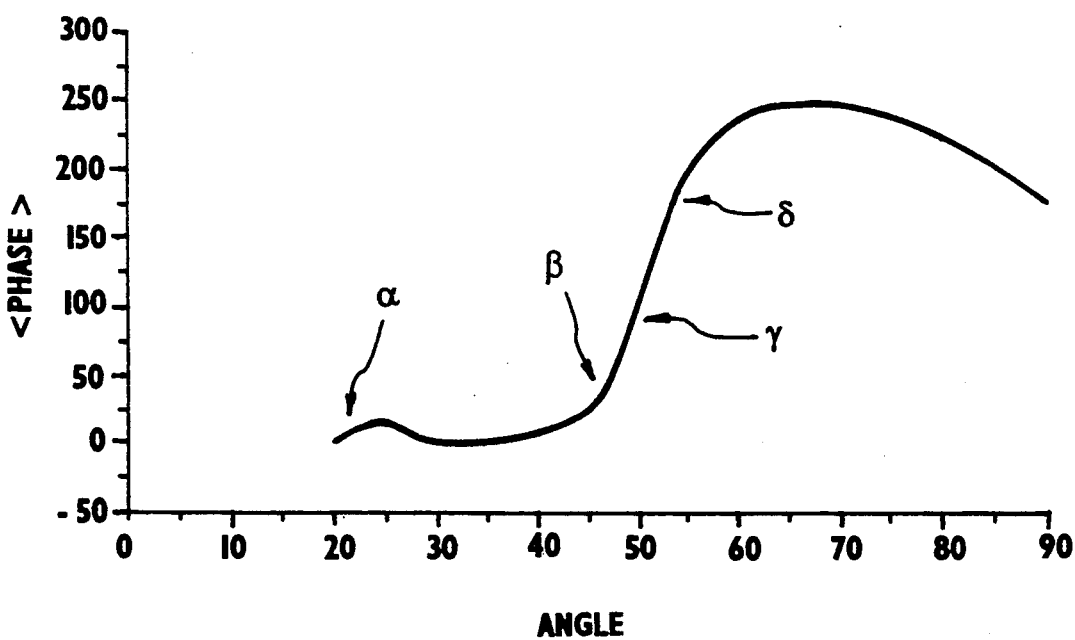
FIG. 7 is a graph of the phase of a reflected ultrasound wave in the method of the present invention as a function of the angle of incidence of the emitted wave.

The general behavior of the amplitude and phase of the ultrasound wave reflected from a bone surface have well identified features which are present in a majority of the samples observed. For example, FIG. 6 shows the magnitude (amplitude) of the reflected signal as a fraction of the magnitude of the incoming beam in water or muscle, and FIG. 7 shows the phase of the signal measured in degrees, in both cases as a function of the angle of incidence. The measurements of FIGS. 6 and 7 came from a bone specimen which had a density of 2 g/ml, a pressure wave velocity of 3974 m/s, and a shear wave velocity of 1987 m/s.

FIG. 6 depicts first edge 80a and second edge 80b, which are generally defined as sharp decreases in amplitude between regions of having a lesser rate of change in amplitude. FIG. 6 also depicts first critical angle 82a and second critical angle 82b. First critical angle 82a can be seen as the first maximum in amplitude as the angle of incidence increases from 0°. The second critical angle 82b is not as easily visible in this drawing. The second critical angle can be either a second maximum in amplitude, or it must be found through an edge, and in this case is the latter.

The phase contains further information on the mechanical properties of the material. Through Snell's law, it can be seen that the angle $\alpha$ in FIG. 7, at which the phase first appreciably differs from zero, identifies the pressure wave velocity, and similarly, the angle $\beta$ in FIG. 7, where the slope of the curve changes abruptly, identifies the shear wave velocity. At the angle $\gamma$, the phase is equal to 90°, and thus allows the determination of the density, whereas at angle $\delta$, a further relationship between $v_s$ and $v_p$ can be used to determine one value when the other is known, using the following formulae:

$$\frac{v_p}{\sqrt{v_p^2 x^2 - 1}} = v_s^3 x^{2} \cdot \frac{\sqrt{v_s^2 x^2 - 1}}{(v_s^2 x^2 - 0.5)^2}$$

An alternate embodiment of the apparatus includes at least one array of receiving transducers and at least one array of emitting transducers positioned along the circumference of an array holder, which preferably forms an arc of 180° or less. In this embodiment, the emitting transducers are operated sequentially one after the other, while the signals from all the receiving transducers are acquired in correspondence to the operation of each emitting transducer. At least the emitting transducer array, and preferentially both arrays, may then be moved in incremental steps in opposing directions along the circumference of the array to improve the angular resolution. At the end of a number of such steps, each transducer in the moving array will be positioned at, or nearly at, the angular position which the adjacent transducer occupied before the movement. In a typical embodiment, the angular distance between two transducers is 8°, and each step moves the array by 0.4°.

EXAMPLE 1

Ultrasound tests were performed using an apparatus (shown in FIG. 8) which consisted of a baseplate 100 containing a water bath 101 with angular graduations and two motor driven arms which carried the ultrasonic transducers 102 and 104 around the circumference of the plate. Adjustments were provided to allow alignment of the transducers so that they were in the same plane and that the transducer axis intercepted the axis of rotation. A removable holder 106 permitted the accurate positioning of the sample 107 with respect to the axis of transducer rotation. This holder also provided three angular degrees of freedom for the sample, allowing its surface normal to be aligned in the plane of the transducers 102 and 104 and providing for rotation of the sample about an axis lying in this plane and intersecting the axis of transducer rotation.

Figure 8:
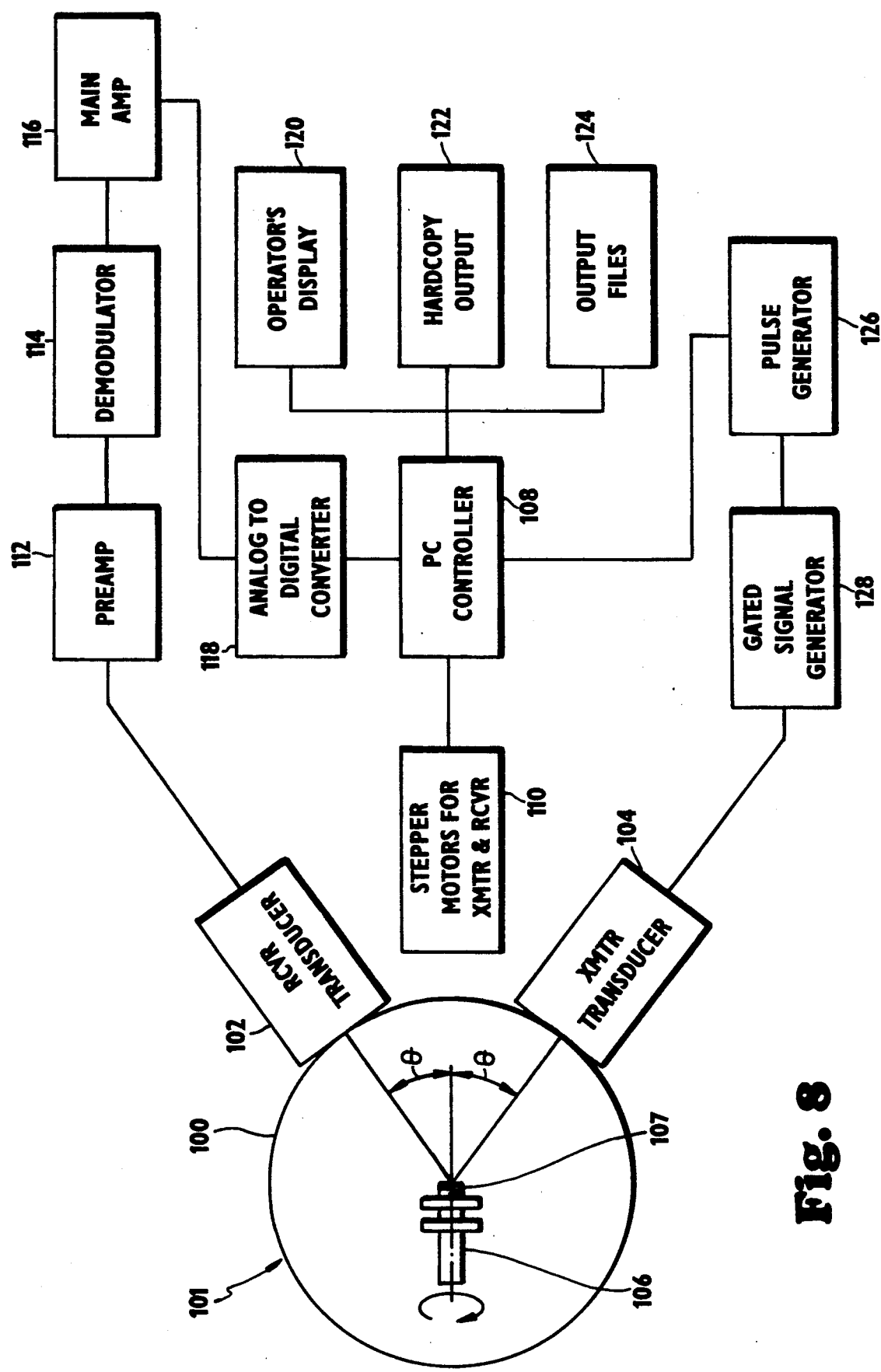
FIG. 8 is a simplified block diagram of the apparatus used in the tests of Example 2.

The data acquisition electronics were based on a microprocessor controller 108, as shown in FIG. 8. Stepping motors 110 controlled by the computer 108 served to position the transducers during data collection: the transducers were synchronously moved to maintain equal but opposite angles with respect to the surface normal of the sample. The processed data were displayed 120 in real time, as a plot of signal amplitude versus transducer angle. A hard copy output 122 was obtained at the time of acquisition, and data was also stored to disk in the form of output files 124 for data reduction.

In operation, a pulse train triggered by a microprocessor 108 (IBM/PC) was used to drive the ultrasonic transmitter 104. This included the use of a pulse generator 126 and a gated signal generator 128. Pulse duration and frequency were manually selected. The transmitter and receiver were a matched pair of transducers with diameters of 13 mm and nominal resonant frequencies of 3.5 MHz. The reflected signal picked up by the receiver 102 was preamplified by preamp 112, and then demodulated by demodulator 114 to produce a unipolar waveform. After subsequent amplification by main amplifier 116 and low-pass filtering, the received signal was presented to an analog-to-digital converter 118 operated in sampling mode. The acquisition software provided for completely digitizing the waveform during alignment, but during actual data collection the sampling time was fixed at an operator-selected point on the incoming waveform.

The transmission measurements discussed here were made at a frequency of 2.25 Mhz. The two spring-loaded transducers, mounted on an adjustable C-arm, were placed in contact with opposite sides of a roughly cubical sample. A small drop of water was used to couple each transducer to the sample. The transit time, $\Delta t$, for a pulsed wave train between the two transducers was then measured with a digital oscilloscope. The pathlength, x, traversed by the wave packet was determined simply by measuring the sample thickness with a micrometer caliper. From the transit time and sample thickness, the ultrasound velocity $V_{tr}$ was calculated from $$V_{tr} = x/\Delta t.$$

Two sets of samples were prepared for this study. The first set consisted of common laboratory materials which were believed to be essentially isotropic and homogeneous. The second set comprised samples of human cortical bone obtained from cadavers. Both sets of samples were tested using both the reflection and the transmission techniques.

Samples of the nine materials listed in Table 1 were fabricated in the form of cubes nominally measuring 10 mm on a side. These cubes were used for transmission measurements. A second group of samples from the same material stock were made in the form of right cylinders with a minimum diameter of 15 mm; these were used in reflection measurements, the end of the cylinder being the surface subjected to analysis. For all materials, velocity measurements using both transmission and reflection were made in two orthogonal directions lying in the selected frontal face of the specimen. This was done for a minimum of three trials on each sample using both techniques, producing at least six velocity values per sample.

Ten cortical bone specimens were machined to produce roughly cubical samples and were stored in a 50% ethanol solution. These cubes were approximately 5 mm on a side. Because the sensitivity of the reflection technique is affected by the flatness of the sample surface, the samples were wet lapped on #600 silicon carbide paper before the reflection measurements. Both transmission and reflection measurements were performed on identical samples. Transmission velocity measurements were made across each pair of opposing faces on the cube. In reflection, three faces of each cube were observed; for each face, the sample was rotated to obtain velocity measurements at 30° increments or less across a range of 360°. When a clear peak in the reflected amplitude was not observable, the critical angle was estimated by comparison with the position of the peak at a closely adjacent orientation (i.e. ±30 degrees).

TABLE 1

| ULTRASOUND VELOCITIES FOR ISOTROPIC MATERIALS | | | | | |
|---|---|---|---|---|---|
| MATERIAL | $V_r$ | $\sigma V_r$ | $V_{tr}$ | $\sigma V_{tr}$ | $Vn^*$ | $Vn^{**}$ |
| Lead | 2153 | 34 | 2252 | 29 | 2160 | |
| Delrin | 2283 | 8 | 2330 | 12 | | 2430 |
| Acrylic | 2670 | 12 | 2692 | 15 | 2670 | |
| Silver | 3653 | 18 | 3695 | 21 | 3636 | 3600 |
| Brass | 4205 | 14 | 4202 | 57 | | |

TABLE 1-continued

| ULTRASOUND VELOCITIES FOR ISOTROPIC MATERIALS | | | | | |
|---|---|---|---|---|---|
| MATERIAL | $V_r$ | $\sigma V_r$ | $V_{tr}$ | $\sigma V_{tr}$ | $Vn^*$ | $Vn^{**}$ |
| Bronze | 4270 | 95 | 4181 | 57 | | |
| Copper | 4625 | 29 | 4642 | 28 | 4760 | 5010 |
| Steel | 5983 | 106 | 5867 | 110 | 5950 | 5900 |
| Aluminum | 6355 | 100 | 6198 | 29 | 6360 | 6420 |

*Moses, The Practicing Scientist's Handbook, Van Nostrand Reinhold Co., pp. 528–29 (1978).
**Selfridge, Approximate Material Properties in Isotropic Materials, IEEE Transactions on Sonics and Ultrasonics, 32:381–394 (1985).

For the isotropic test materials, the velocities obtained by the two methods were in excellent qualitative agreement with each other. Table 1 shows that the two methods gave rather close values of the velocities between 2200 and 6300 meters per second (m/s) and that both sets were in substantial agreement with published data for the same materials. A linear fit to the reflection vs. transmission data produced a regression line with an $R^2$ of 0.9993. Even though the fitted slope was significantly different from unity, the ratio of the two velocities had an average value of 1.00±0.02. The largest disagreements—the worst case difference was 160 m/s—were observed at the ends of the velocity range. The differences were significantly greater than the statistical errors and we attribute them both to heterogeneities in the materials and to residual instrumental inaccuracies. In the more limited range encompassing cortical and cancellous bone velocities (3000 to 4500 m/s) the differences between the two sets of values were less than 1%.

In the cortical bone tests, the reflected amplitude off a typical cortical bone sample showed a distinct maximum peak, allowing a precise measurement of the critical angle. A sharp fall in amplitude curves obtained in scans at adjacent orientations was used to better identify the peak position when it was not sufficiently distinct. When the angle of orientation was changed, the corresponding velocity showed a distinct periodic dependence on orientation. The principal axes were identified through the position of the maxima and minima in such curves: in 19 of the 29 faces these axes coincided with the edges of the sample to within 15 degrees, but in 10 out of 29 they differed by at least 30 degrees.

The reflection technique gave velocities consistently higher than the transmission technique, although the two distributions were strongly correlated. The ratio between the reflection velocity and the transmission velocity was 1.12±0.04, leading to a difference of 434±128 m/s.

Such a result is not unexpected in this dispersive medium because the two methods operate at different frequencies. In addition, there are important differences intrinsic to the two methods. In particular, while the reflection technique measures velocities along the surface of a specimen, the transmission technique measure them through the interior volume as well. Thus material heterogeneities, structural geometry and density variations affect the two methods differently.

EXAMPLE 2

Figure 9:
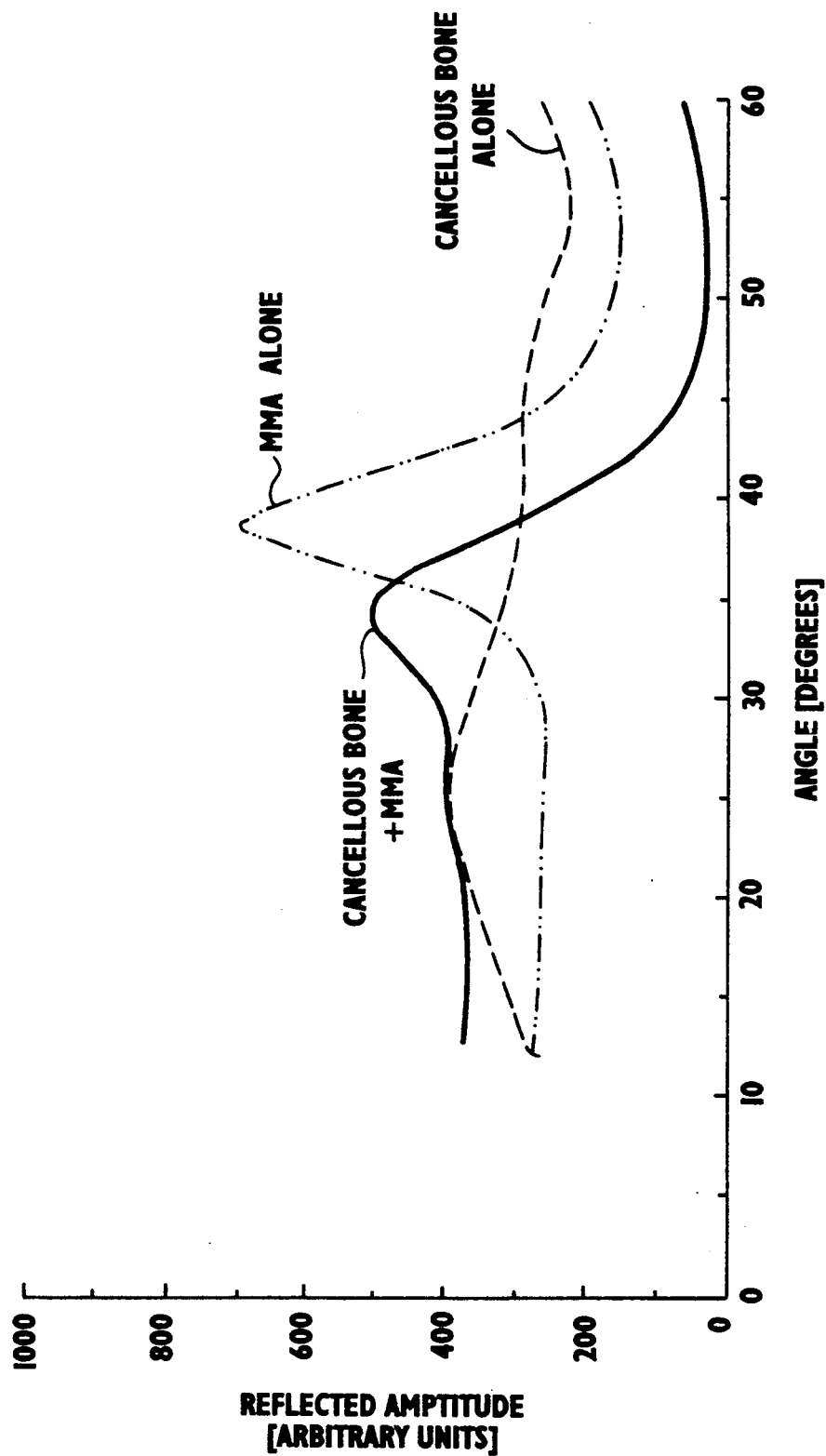
FIG. 9 is a graph of reflected ultrasound wave amplitude vs. angle of incidence in samples that are and are not saturated with MMA plastic.

Cancellous bone samples were obtained from biopsies, the samples were saturated with methylmethacrylate, and amplitude of reflected ultrasound waves was determined as a function of angle of incidence. While the magnitude of the reflected amplitude was profoundly affected by the addition of MMA, the position of the critical angle remained fixed, as shown in FIG. 9. Under these conditions, the method of the present invention measures the properties of the trabeculae in the region under study.

Successive measurements made by rotating the sample around its surface normal revealed the inherent orthorhombic symmetry of bone: minima and maxima are separated by 90° and the pattern repeats itself regularly.

EXAMPLE 3

A study was performed in 16 patients who had osteoporosis and at least one vertebral compression fracture. The patient population comprised 12 women and four men with a mean age of 56 years (range 28–78 years). Eleven women were postmenopausal and one had early oophorectomy. The four men had idiopathic osteoporosis. None of the patients had hyperadrenocorticism, primary hyperparathyroidism, renal tubular acidosis, thyrotoxicosis, multiple myeloma, renal failure, or liver disease, and none had a prior history of taking anticonvulsants, glucocorticoids, estrogens, fluoride, calcitonin, excessive amounts of alcohol, or pharmacological doses of vitamin D preparations. None had active peptic ulcer disease. None of the men had hypogonadism.

All patients received cyclical fluoride treatment. Twelve patients received slow release sodium fluoride (Slow Fluoride, Mission Pharmacal Co., San Antonio, Tex.), 25 mg twice daily, 50 $\mu$g 25-OHD twice weekly and sufficient calcium supplementation (as calcium citrate in divided doses) to bring the daily calcium intake to 1500 mg/day for 3 months. The cycle was concluded by 6 weeks of 25-OHD and calcium supplements at the same dosages without fluoride. Each patient completed four such cycles for a total treatment interval of 20 months. The remaining four patients took slow release sodium fluoride 25 mg with calcium citrate 400 mg calcium before breakfast and at bedtime for 12 months, and then discontinued fluoride for one month while maintaining calcium citrate supplementation. The cycle was then repeated so that each patient received this treatment regimen for 26 months.

Two full thickness transcortical iliac crest bone biopsies were obtained from each patient prior to beginning the study and again at the completion of treatment (toward the end of withdrawal period, corresponding to 20 months in the first 12 patients, and 26 months in the remaining four patients). Biopsies were obtained on opposite sides in each patient. Ultrasound data from the two groups of patients were indistinguishable; thus, they were combined in this report. Specimens were examined by the reflection ultrasound method of the present invention. In addition, each patient underwent measurement of bone density of the second, third, and fourth lumbar vertebrae at the beginning of the study and at the completion of each cycle by dual photon absorptiometry (Lunar Radiation, Madison, Wis.).

Successive ultrasound measurements were made by rotating the sample around its surface normal. A fit to the entire distribution allowed the identification of velocities along two orthogonal, principal axes. Critical angle velocities were measured at 5–7 orientations in each biopsy sample. Overall, there were 107 determinations on 16 pre-treatment samples, and 100 determinations on 16 post-treatment samples. There were 70 matched pairs, where a critical angle velocity was available before and after treatment from the same patient at the identical orientation. Previous studies indicated that while the magnitude of the reflected amplitude is affected by methylmethacrylate impregnation, the position of the critical angle remains fixed. Under these conditions the method is sensitive to the properties of the trabeculae in the region under study.

Data are presented as mean$\pm$SEM. Statistical difference in ultrasound conduction velocity at all angles of orientation before and following intermittent sodium fluoride therapy was performed by the Wilcoxon Rank Sum Test. For paired observation, two-tailed paired t-test was used to show a significant change produced by treatment. Correlation between the change in one mineral density and ultrasound conduction velocity was determined by univariate linear regression analysis.

Figure 10A:
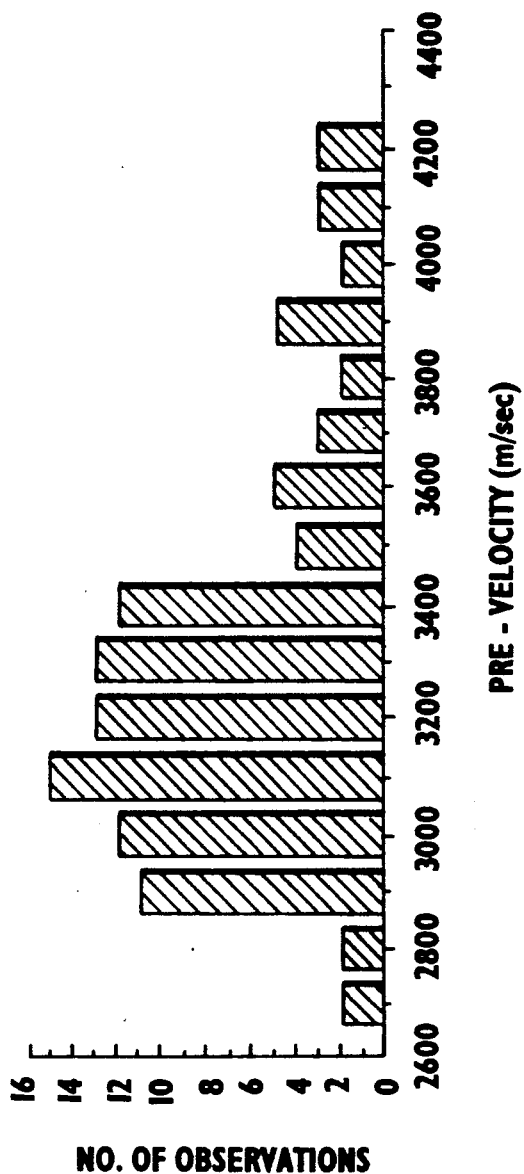
FIG. 10 is a histogram of the distribution of ultrasound velocities in bone biopsy specimens (A) before and (B) following two years of intermittent slow-release fluoride therapy.
Figure 10B:
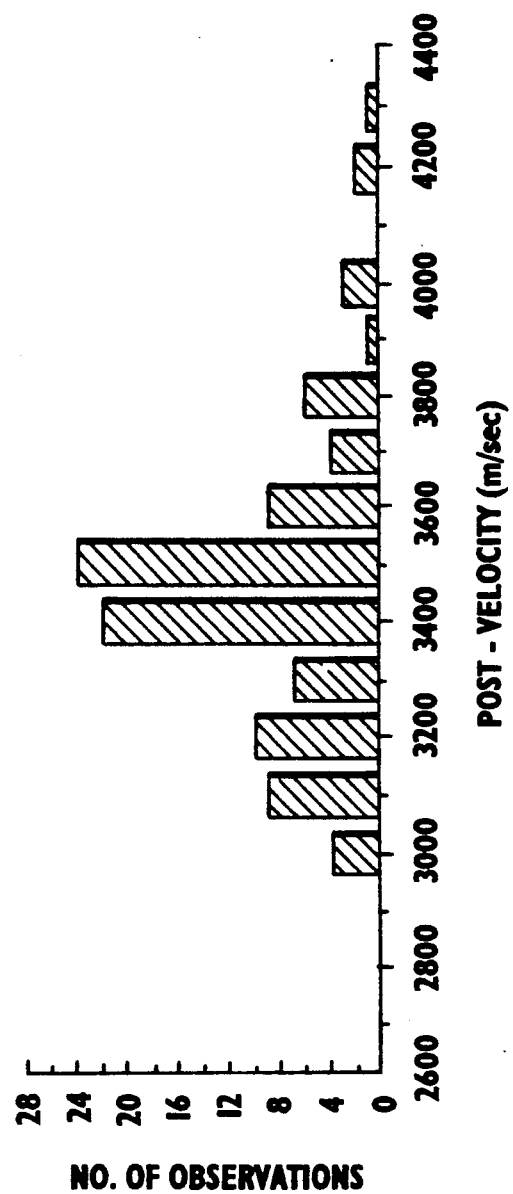

FIG. 10 summarizes the distribution of ultrasound velocities prior to and following intermittent fluoride therapy at all orientations for all sixteen patients. Prior to therapy (part A of FIG. 10), ultrasound velocities ranged from 2700 m/sec to as high as 4200 m/sec. However the majority of the values were below 3400 m/sec with the peak at 3500 m/sec. The mean ultrasound velocity increased from 3336$\pm$33 m/sec before treatment (n=107) to 3496$\pm$26 m/sec following treatment (n=100) (p=0.0001).

Figure 11:
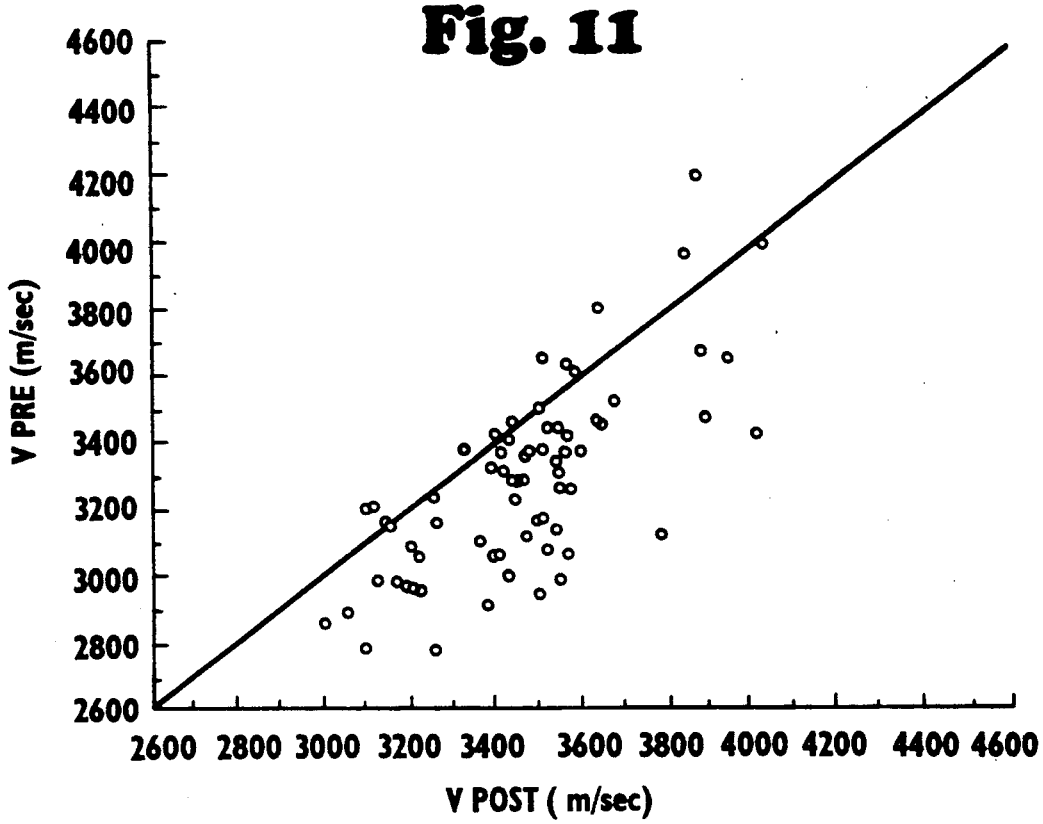
FIG. 11 is a comparison of pre- versus post-treatment ultrasound velocities in bone biopsy specimens from 16 patients before and after two years of intermittent slow-release fluoride therapy. Measurements for each angle of specimen orientation are plotted. The solid line represents the line of identity whereby points above and below the line represent negative and positive responses respectively.

FIG. 11 depicts the relationship between pre- and post-treatment ultrasound critical angle velocities for 70 matched pairs from 16 patients. As shown in this figure, 80% of the paired determinations demonstrated a shift towards higher conduction velocities following therapy.

Figure 12:
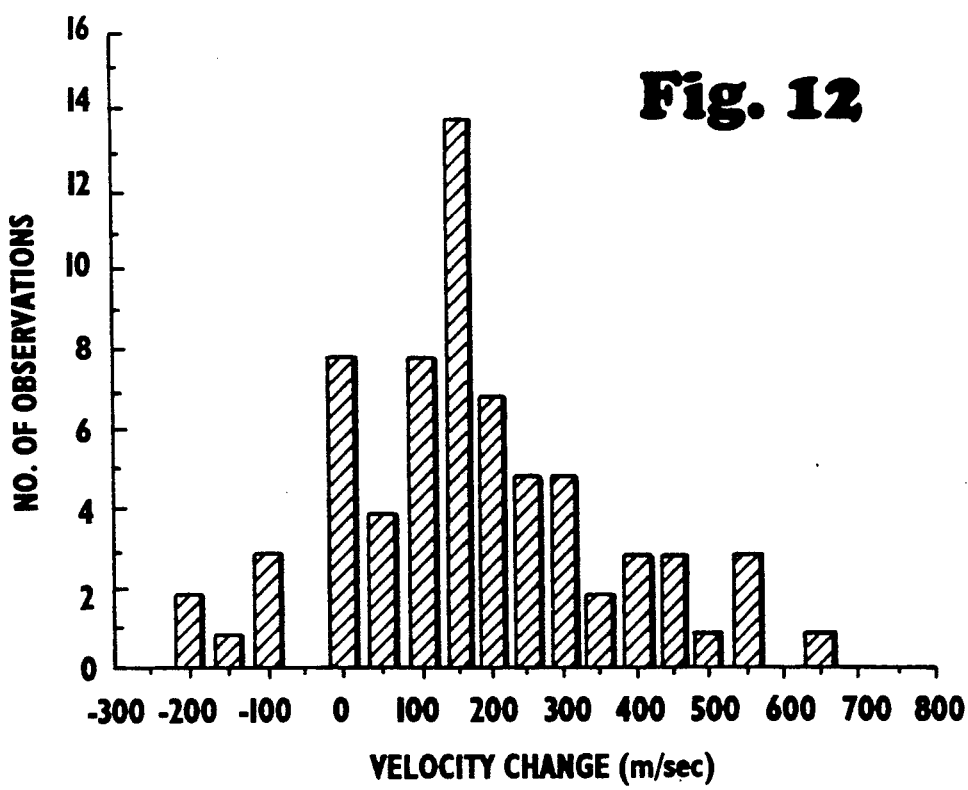
FIG. 12 is a histogram of the change in ultrasound velocity in bone biopsy specimens following two years of intermittent slow-release fluoride therapy.

A histogram of the changes in ultrasound velocities for all the paired observations at different orientations is summarized in FIG. 12. Of the 70 paired observations, 56 demonstrated an increase in ultrasound conduction velocity following intermittent fluoride continuous calcium citrate therapy. Fourteen observations demonstrated no increase or a slight decrease in velocity. Overall, the mean increase of 163 m/sec was significant by two-tailed paired t analysis (p=0.001).

Although bone mineral content (BMC) of the spine also increased during the treatment period (6.9$\pm$1.0%), there was no correlation between the percent change in bone mineral content and the percent change in mean ultrasound velocity for the sixteen patients (r=0.014, p=0.958). See FIGS. 13 and 14.

Since higher velocities are directly correlated with improved biomechanical properties of cancellous bone, the increase in velocity observed here is consistent with improved mechanical strength of bone specimens.

EXAMPLE 4

A clinical prototype of apparatus in accordance with the present invention which employs an electronically-activated array of ultrasound transducers was tested in 92 subjects. This population was divided into five groups:

TABLE 2

| Number and age of the subjects in the five patient groups | | | | | |
|---|---|---|---|---|---|
| group | young normal | control | osteoporotic untreated | osteoporotic treated | treated recurrent |
| number | 17 | 23 | 21 | 27 | 4 |
| age | 39 | 75 | 68 | 68 | 77 |
| $\pm$s.e. | 2 | 2 | 3 | 2 | 5 |

The ulna of the non-dominant arm of each subject was chosen as the site for simultaneous determinations of bone mineral density and of velocity, the results of which are shown in Table 3. With the technique of the present invention it has been possible for the first time to measure separately and independently both cancellous and cortical bone velocities; bone mineral densities ("BMD") were obtained at the head of the ulna (to estimate cancellous bone density) and at its distal ⅓ (cortical bone density) and for the lumber vertebrae (L2-L4).

TABLE 3

Velocities and bone mineral densities in four patient groups (means ± standard errors of the mean).

| | young normal | control | osteo-porotic untreated | osteo-porotic treated | treated recurrent |
|---|---|---|---|---|---|
| canc. velocity m/s ± s.e. | 3306 43 | 3156 25 | 2870 49 | 3100 36 | 2886 87 |
| cort. velocity m/s ± s.e. | 4100 41 | 4040 57 | 4069 40 | 4155 38 | 4064 122 |
| ulna canc. bmd g/cm² ± s.e. | 0.311 .014 | 0.245 .008 | 0.237 .012 | 0.247 .008 | 0.214 .02 |
| vertebral bmd g/cm² ± s.e. | 1.07 .04 | 0.94 .028 | 0.838 .054 | 0.733 .03 | 0.648 .035 |

Both velocity and bone mineral density decrease with age, as seen by comparing the first two columns (young normal and control subjects). An unpaired t-test comparison shows that the decrease in cancellous bone with aging is significant at the p=0.004 level, a significance comparable with the decrease in vertebral BMD, p=0.009. Osteoporosis results in a further drop of the cancellous bone velocity and of the lumbar density, but the other quantities remain essentially unaltered, as seen by comparing the second column (control) with the third (osteoporotic). The difference in velocity between the control group and untreated osteoporotic patients is significant at the 0.0001 level, whereas for BMD p=0.097. Slow-release NaF and calcium citrate treatment restores the loss in cancellous bone velocity, as seen by comparing the third and fourth column, with p=0.003. The lower value of lumbar bone mineral density reflects the fact that the patients in the treated group were originally selected with more severe osteopoenia. The difference in velocity between recurrent and fracture-free patients (last two columns) is significant at the 0.035 level, although no significant differences are observed in BMD.

TABLE 4

Unpaired t-tests for velocity differences (first–second).

| | normal >50 vs <50 | osteoporotic vs control | treated vs untreated | recurrent vs treated |
|---|---|---|---|---|
| canc. velocity | −150 p = 0.004 | −286 0.0001 | +230 0.0003 | −214 0.04 |
| vertebral BMD | −0.13 p = 0.009 | −0.10 0.10 | (−.11) (0.09) | −0.08 0.26 |

The changes in cancellous bone velocity are highly significant. The cancellous bone velocity measured by the technique of the present invention in the head of the ulna is sensitive to aging, discriminates between the effects of aging and the presence of osteoporosis, changes after treatment, and appears to differentiate between fracture-free and recurrent treated patients.

This holds true even when the subjects are age-matched. Patients were paired so that changes in the BMD and age from group to group were minimal: a paired t-test then shows that in osteoporotic patients the cancellous bone velocity decreased by 308 m/s with respect to the control group, a result significant at the 0.005 level. After treatment the velocity increased by 284 m/s (p=0.02) if the treatment was successful, but did not increase if vertebral fractures recur.

Figure 13:
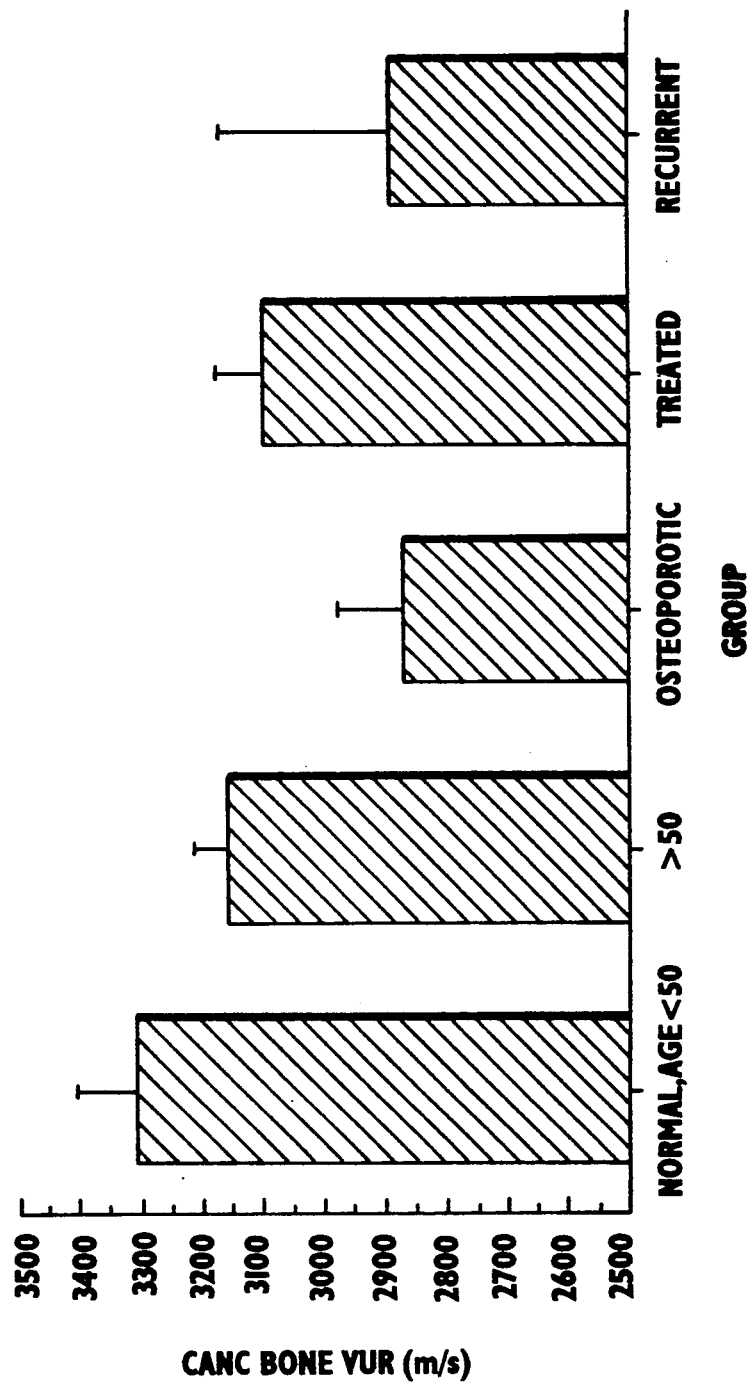
FIG. 13 shows the mean and 95% confidence levels for ultrasound velocity in cancellous bone in five groups of subjects.
Figure 14:
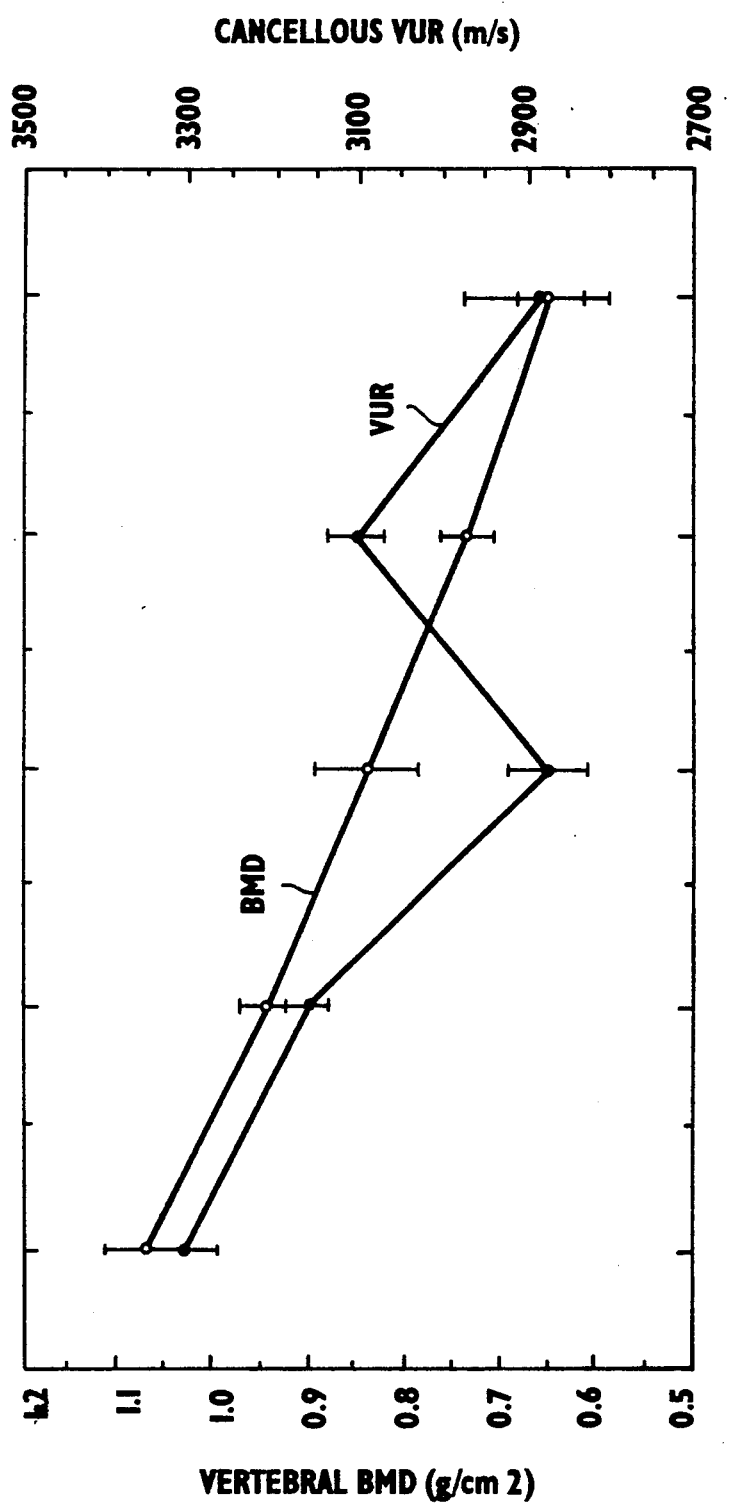
FIG. 14 shows the mean values and standard errors of velocity (solid dots) and vertebral bone mineral density (open dots) (BMD) in five patient groups.

We note that average cancellous bone velocities observed in vivo in the ulna are slightly smaller (by about 200 m/s) than those previously measured in iliac crest biopsies, but the change in velocity after treatment is equal to that previously determined in consecutive biopsies from the same patient. The mean value and 95% confidence level intervals for vertebral BMD and cancelleous bone ultrasound velocity are shown in FIG. 13 and FIG. 14.

The behavior if the cancellous bone velocity is largely independent of that of the BMD. There is at most a weak relationship between cancellous bone velocity and bone mineral density, measured either in the vertebral body or the head of the ulna. In both cases, the coefficient of correlation is $r^2=0.21$.

The significance of cancellous bone velocity in the assessment of osteoporosis is indicated by the fact that the decrease in velocity due to the presence of osteoporosis is greater than that due to aging. Furthermore, the increase in velocity after treatment with slow release NaF correlates with the success of therapy. Conversely, in patients with recurrent fractures, no increase in velocity is observed. The cortical bone velocity, in contrast, shows only minor fluctuations with aging and disease. However, our results indicate a modest increase after therapy, inconsistent with the hypothesis that cortical bone velocity decreases posttreatment.

In conclusion, the cancellous bone velocity measured by high frequency ultrasound with the reflection technique is an intrinsic mechanical property of bone material. This quality index is profoundly affected by osteoporosis. Although independent of bone density, the index correlates with response to therapy, as delineated by the presence or absence of recurrent vertebral fractures.

The present invention permits the use of velocities measured by ultrasound to assess the result of osteoporosis therapy. An increase in pressure wave velocity indicates that the treatment has had a positive effect; such an increase is diagnostic of improvement in the material properties at the trabecular level. This is to be distinguished from the measurement of mere structural properties of an entire piece of bone, which would not necessarily reveal an improvement in an individual component of bone. Constant or decreasing pressure wave velocity indicates failure of the treatment. In effect, the present invention enables doctors to assess more accurately and quickly the results of therapy for osteoporosis.

To summarize some of the other findings of the present invention:

1. the sound velocity of bone material is an index of intrinsic bone strength;

2. high frequency ultrasound—in reflection or transmission—determines that velocity ($f>1$ MHz) but low frequency ultrasound ($f<0.1$–$0.5$ MHz) does not;

3. the velocity of sound at the material level correlates with the material density;

4. the velocity of sound at the structural level correlates with structural density;

5. low frequency ultrasound must be used to measure that velocity;

6. the velocity of sound at the material level can be measured noninvasively, in vivo, e.g. in the ulna of the nondominant (typically, left) arm;

7. the strength of bone depends both upon the total amount of bone present (its structural density) and the material quality of bone (its material velocity); and 8. if the cancellous bone velocity in the ulna measured with the present invention is <3000 m/s, it is likely that vertebral fractures will occur, while if v>3100 m/s, it is unlikely that fractures will occur.

The preceding description is intended to illustrate specific embodiments of the present invention, but is not intended to provide an exhaustive list of all impossible embodiments of the invention. Those skilled in this field will recognize that variations and modifications could be made which would remain within the scope of the present invention.

We claim:

1. Apparatus for investigating the mechanical properties of a solid material, including:
   means for positioning the apparatus in proximity to a surface of a solid material;
   at least one emitting ultrasound transducer positioned for emitting an ultrasound wave towards a surface of the material;
   at least one receiving ultrasound transducer positioned for receiving an ultrasound wave that has been emitted and has contacted the surface of the material;
   means for varying the angle of incidence of the emitted ultrasound wave towards the surface of the material;
   means responsive to the received ultrasound wave for determining the alignment of the surface of the material with respect to the emitting and receiving ultrasound transducers; and
   signal analyzer means coupled to the at least one receiving ultrasound transducer for determining at least one characteristic of the received ultrasound wave which is indicative of a mechanical property of the material.

2. The apparatus of claim 1, further comprising means for varying the emitting plane which is defined by the emitted ultrasound wave and the normal to the surface of the material at the location where the ultrasound wave has contacted the surface of the material.

3. The apparatus of claim 2, where the means for varying the emitting plane include a stepper mechanism coupled to the transducers, which stepper mechanism comprises means for moving and positioning the transducers in relation to the material.

4. The apparatus of claim 1, where the at least one receiving ultrasound transducer is positioned to receive an ultrasound wave that has been reflected from the surface of the material.

5. The apparatus of claim 4, where the signal analyzer means is operable to determine the amplitude of the reflected ultrasound wave as a function of the angle of incidence.

6. The apparatus of claim 5, where the signal analyzer means comprises means for determining at least one edge in which the amplitude of the reflected ultrasound wave decreases rapidly as a function of the angle of incidence between two regions of slower variability.

7. The apparatus of claim 4, where the signal analyzer means comprises means for determining the phase of the reflected ultrasound wave as a function of angle of incidence.

8. The apparatus of claim 7, where the signal analyzer means is also operable to determine at least one angle of incidence at which the phase of the reflected ultrasound wave first appreciably deviates from zero as that angle increases from 0°.

9. The apparatus of claim 1, where the at least one receiving ultrasound transducer is positioned to receive an ultrasound wave that has been transmitted through the material.

10. The apparatus of claim 9, where the signal analyzer means comprises means for determining the amplitude of the transmitted ultrasound wave as a function of the angle of incidence.

11. The apparatus of claim 10, where the signal analyzer means comprises means for determining maxima and minima in the amplitude of the transmitted ultrasound wave as a function of the angle of incidence.

12. The apparatus of claim 1, where the signal analyzer means comprises means for determining at least one characteristic of the received ultrasound wave selected from the group consisting of amplitude and phase.

13. The apparatus of claim 1, where the means for varying the angle of incidence include a stepper mechanism coupled to the transducers, which stepper mechanism comprises means for moving and positioning the transducers in relation to the material.

14. The apparatus of claim 1, where the apparatus includes an array of transducers, said array comprising the at least one emitting ultrasound transducer and the at least one receiving ultrasound transducer.

15. The apparatus of claim 14, where the array of transducers is in the form of a semicircular array.

16. The apparatus of claim 14, where the array of transducers is in the form of a hemispherical array.

17. The apparatus of claim 14, where the means for varying the angle of incidence include a switching circuit for selectably operating at least one transducer in the array as an emitting transducer.

18. The apparatus of claim 14, where the means for varying the angle of incidence include a switching circuit for selectably operating at least one transducer in the array as a receiving transducer.

19. The apparatus of claim 1, where the material is bone.

20. The apparatus of claim 19, where the signal analyzer means comprises means for approximating the velocity of a pressure wave in the bone based on a first critical angle corresponding to a first maxima in amplitude encountered as the angle of incidence increases in the range of 0°-90°.

21. The apparatus of claim 20, where the signal analyzer means comprises means for approximating the velocity of a shear wave in the bone based on a second critical angle corresponding either to a second maxima in amplitude followed by a deep minimum or to an inflection point in amplitude following a deep minimum and encountered after the first maxima as the angle of incidence increases in the range of 0°-90°.

22. The apparatus of claim 19, where the apparatus includes a liquid-filled bag which has at least one surface that is flexible and which can be positioned on the surface of a patient's body in proximity to a bone, and where the ultrasound transducers are in acoustic contact with the liquid in the bag.

23. Apparatus for investigating the mechanical properties of bone, including:
- a liquid-filled bag which has at least one surface that is flexible;
- an array of ultrasound transducers which are in acoustic contact with the liquid in the bag, and which include switching means for selectably operating at least one transducer in the array as an emitting ultrasound transducer positioned for transmitting an ultrasound wave towards a surface of the bone, and for selectably operating at least one ultrasound transducer in the array as a receiving ultrasound transducer positioned for receiving ultrasound waves reflected by the surface of the bone;
- means for varying the angle of incidence of the emitted ultrasound wave towards the surface of the bone;
- means for varying the emitting plane which is defined by the emitted ultrasound wave and the normal to the surface of the bone; and
- signal analyzer means coupled to the array of ultrasound transducers, which receive the reflected ultrasound wave and are operable to determine at least one characteristic of the reflected ultrasound wave as a function of the angle of incidence, and from that to estimate the strength of the bone.

24. The apparatus of claim 23, where the signal analyzer means comprises means for determining the phase of the reflected ultrasound wave as a function of the angle of incidence.

25. A method of investigating the mechanical properties of a material, including the steps of:
a. emitting an ultrasound wave to impinge a surface of a material at an angle of incidence;
b. receiving the ultrasound wave after it has contacted the material;
c. determining the normal to the surface of the material by analyzing the received ultrasound waves generated when the emitted ultrasound wave impinges the material from each of a plurality of varying directions; and
d. determining a characteristic of the received ultrasound wave at each of a plurality of varying angles of incidence in the range of 0°–90°, and in a plurality of varying emitting planes defined by the emitted ultrasound wave and the normal to the surface of the material, and using that characteristic to estimate a mechanical property of the material.

26. The method of claim 25, where the characteristic in step d is selected from the group consisting of amplitude and phase of the received ultrasound wave.

27. The method of claim 25, where the ultrasound wave is received after reflecting from the surface of the material.

28. The method of claim 27, where step d includes determining the amplitude of the reflected ultrasound wave as a function of the angle of incidence.

29. The method of claim 28, where step d also includes determining at least one edge in which the amplitude of the reflected ultrasound wave decreases rapidly as a function of the angle of incidence between two regions of slower variability.

30. The method of claim 27, where step d includes determining the phase of the reflected ultrasound wave as a function of angle of incidence.

31. The method of claim 30, where step d also includes determining at least one angle of incidence at which the phase of the reflected ultrasound wave first appreciable deviates from zero as the angle is increased from 0°.

32. The method of claim 25, where the ultrasound wave is received after being transmitted through the material.

33. The method of claim 32, where step d includes determining the amplitude of the transmitted ultrasound wave as a function of the angle of incidence, and determining maxima and minima in the amplitude.

34. The method of claim 25, where the material is bone.

35. The method of claim 34, where step d includes approximating the velocity of a pressure wave in the bone based on a first critical angle corresponding to a first maxima in amplitude encountered as the angle of incidence increases in the range of 0°–90°.

36. The method of claim 35, where step also includes approximating the velocity of a shear wave in the bone based on a second critical angle corresponding either to a second maxima in amplitude followed by a deep minimum or to an inflection point in amplitude following a deep minimum and encountered after the first maxima as the angle of incidence increases in the range of 0°–90°.

37. The method of claim 36, where step d includes computing the shear wave velocity ($v_s$) using the relationship:

$$v_s = \frac{c}{\sin\phi_2}$$

where c is the velocity of the transmitted ultrasound wave (I) in the medium adjacent the bone and $\phi_2$ is the angle of incidence at the second critical angle.

38. The method of claim 35, where step d includes computing the pressure wave velocity ($v_p$) using the relationship:

$$v_p = \frac{c}{\sin\phi_1}$$

where c is the velocity of the transmitted ultrasound wave in the medium adjacent the bone and $\phi_1$ is the angle of incidence at the first critical angle.

* * * * *

UNITED STATES PATENT AND TRADEMARK OFFICE
CERTIFICATE OF CORRECTION

PATENT NO. : 5,197,475
DATED : March 30, 1993
INVENTOR(S) : Antich et al

It is certified that error appears in the above-indentified patent and that said Letters Patent is hereby corrected as shown below:

At column 17, line 26, just below the lines that read:

```
"ulna canc.      0.311      0.245      0.237      0.247      0.214
bmd g/            .014       .008       .012       .008       .02
cm² ± s.e."
``` and just above the lines that read:

```
"vertebral       1.07       0.94       0.838      0.733      0.648
bmd g/            .04        .028       .054       .03        .035
cm² ± s.e."
``` insert the following:

```
--ulna cort. bmd  0.563      0.423      0.455      0.409      0.356
g/cm² ± s.e.      .012       .015       .018       .015       .004      --
```

Signed and Sealed this

First Day of February, 1994

Attest:

BRUCE LEHMAN

*Attesting Officer*    *Commissioner of Patents and Trademarks*